United States Patent [19]

Makrides et al.

[11] Patent Number: 5,552,300

[45] Date of Patent: Sep. 3, 1996

[54] T CELL ANTIGEN RECEPTOR V REGION PROTEINS AND METHODS OF PREPARATION THEREOF

[75] Inventors: Savvas C. Makrides, Bedford; Patrick C. Kung, Brookline, both of Mass.

[73] Assignee: T Cell Sciences, Inc., Needham, Mass.

[21] Appl. No.: 181,492

[22] Filed: Jan. 13, 1994

[51] Int. Cl.$^6$ ............................ C12N 15/00; C12N 15/13
[52] U.S. Cl. .................. 435/69.1; 435/252.3; 435/320.1
[58] Field of Search .............................. 435/69.1, 320.1, 435/252.3

[56] References Cited

U.S. PATENT DOCUMENTS

| | | | |
|---|---|---|---|
| 4,713,332 | 12/1987 | Mak | 435/70 |
| 4,845,026 | 7/1989 | Kung et al. | 435/5 |
| 4,873,190 | 10/1989 | Saito et al. | 435/172.3 |
| 5,024,940 | 6/1991 | Brenner et al. | 435/69.1 |
| 5,185,250 | 2/1993 | Brenner et al. | 435/69.3 |
| 5,212,091 | 5/1993 | Diaz-Collier et al. | 435/69.6 |
| 5,216,132 | 6/1993 | Basi | 530/387.3 |
| 5,223,426 | 6/1993 | Skibbens et al. | 435/240.47 |

FOREIGN PATENT DOCUMENTS

| | | |
|---|---|---|
| 0174366B1 | 3/1986 | European Pat. Off. . |
| 0296786A1 | 12/1988 | European Pat. Off. . |
| WO88/00209 | 1/1988 | WIPO . |
| WO89/03996 | 5/1989 | WIPO . |
| WO90/11294 | 10/1990 | WIPO . |
| WO90/14068 | 11/1990 | WIPO . |
| WO91/09623 | 7/1991 | WIPO . |
| WO93/10438 | 7/1991 | WIPO . |
| WO91/17268 | 11/1991 | WIPO . |
| WO92/02629 | 2/1992 | WIPO . |
| WO92/21367 | 12/1992 | WIPO . |
| WO93/06135 | 4/1993 | WIPO . |

OTHER PUBLICATIONS

Kozak. 1987. Mol. Cell. Biol. 7: 3438–3445.
Brosius et al. 1981. Plasmid 6: 112–118.
Plaza et al. 1991. J. Immunol. 147: 4360–4365.
Sambrook et al. 1989. *Molecular Cloning: A Laboratory Manual*, Second Ed., p. 1.13.
Mulligan et al. 1985. J. Biol. Chem. 260: 3529–3538.
Brosius et al. 1985. J. Biol. Chem. 260: 3539–3541.
Morioka-Fujimoto et al. J. Biol. Chem. 266: 1728–1732.
Hughes et al. 1991. Abstr. Gen. Meet. Am. Soc. Microbiol. 91 Meet.: 258.
Sun, Deming, "Synthetic Peptides Representing Sequence 39 to 59 of Rat Vβ8 TCR Fail to Elicit Regulatory T Cells Reactive with Vβ8 TCR on Rat Encephalitogenic T Cells", Cell. Immunol. 141:200–210 (1992).
Offner, et al., "T Cell Receptor Peptide Therapy Triggers Autoregulation of Experimental Encephalomyelitis", Science, 251:430–432 (1991).
Howell, et al., "Vaccination Against Experimental Allergic Encephalomyelitis with T Cell Receptor Peptides", Science, 246:668–670 (1989).

Hashim, et al., "Spontaneous Development of Protective Anti–T Cell Receptor Autoimmunity Targeted Against a Natural EAE–Regulatory Idiotope Located Within the 39–59 Region of the TCR–Vβ8.2 Chain", J. Immunol. 149:2803–2809 (1992).
Vandenbark, et al., "Immunization with a Synthetic T–Cell Receptor V–region Peptide Protects Against Experimental Autoimmune Encephalomyelitis", Nature, 341:541–544 (1989).
Janeway, Charles A. "Immunotherapy by Peptides?", Nature, 341:482–483 (1989).
Sun, et al., "Suppression of Experimentally Induced Autoimmune Encephalomyelitis by Cytolytic T—T Cell Interactions", Nature 332:843–845 (1988).
Lider, et al., "Nonencephalitogenic CD4—CD8—Vα2Vβ8.2$^+$ Anti–Myelin Basic Protein Rat T Lymphocytes Inhibit Disease Induction", J. Immunol. 147:1208–1213 (1991).
Zaller, et al., "Prevention and Treatment of Murine Experimental Allergic Encephalomyelitis with T Cell Receptor Vβ–Specific Antibodies," J. Exp. Med. 171:1943–1955 (1990).
Owhashi and Katz, "Protection from Experimental Allergic Encephalomyelitis Conferred by a Monoclonal Antibody Directed Against a Shared Idiotype on Rat T Cell Receptors Specific for Myelin Basic Protein," J. Exp. Med. 168:2153–2164 (1988).
MacFerrin, et al., "Overproduction and Dissection of Proteins by the Expression–Cassette Polymerase Chain Reaction", Proc. Natl. Acad. Sci. USA 87:1937–1941 (1990).
Bukrinsky, et al., "Multicopy Expression Vector Based on Temperature–Regulated lac Repressor: Expression of Human Immunodeficiency Virus env Gene in *Escherichia coli*", Gene, 70:415–417 (1988).
Davodeau, et al., "Secretion of Disulfide–Linked Human T–Cell Receptor γδ Heterodimers", J. Biol. Chem. 268:15455–15460 (1993).
Hoo, et al., "Characterization of a Single–Chain T–Cell Receptor Expressed in *Escherichia coli*", Proc. Natl. Acad. Sci. USA, 89:4759–4763 (1992).
Gascoigne, Nicholas R. J., "Transport and Secretion of Truncated T Cell Receptor β–Chain Occurs in the Absence of Association with CD3", J. Biol. Chem., 265:9296–9301 (1990).
Lin, et al., "Expression of T Cell Antigen Receptor Heterodimers in a Lipid–Linked Form", Science, 249:677–679 (1990).
Gregoire, et al., "Engineered Secreted T–Cell Receptor αβ Heterodimers", Proc. Natl. Acad. Sci. USA, 88:8077–8081 (1991).

(List continued on next page.)

*Primary Examiner*—Marianne P. Allen
*Assistant Examiner*—Elizabeth C. Kemmerer
*Attorney, Agent, or Firm*—Banner & Allegretti, Ltd.

[57] ABSTRACT

The present invention relates to the production of full length T cell antigen receptor V region proteins. The invention provides for methods of expressing the proteins as well as expression vectors for enhanced production of V region proteins. The invention further provides for the Vβ5.3 region protein. The proteins of the invention have uses in the diagnosis and therapy of immune disorders.

30 Claims, 2 Drawing Sheets

OTHER PUBLICATIONS

Weber, et al., "Specific Low-Affinity Recognition of Major Histocompatibility Complex Plus Peptide by Soluble T-Cell Receptor":, Nature, 356:793-796 (1992).

Ward, et al., "Binding Activities of a Repertoire of Single Immunoglobulin Variable Domains Secreted from *Escherichia coli*" Nature, 341:544-546 (1989).

Ward, E. S., "Expression and Secretion of T-Cell Receptor Vα and Vβ Domains Using *Escherichia coli* as a Host", Scand. J. Immunol., 34:215-220 (1991).

Ward, E. Sally, "Secretion of T Cell Receptor Fragments from Recombinant *Escherichia coli* Cells", J. Mol. Biol. 224:885-890 (1992).

Novotny, et al., "A Soluble, Single-Chain T-Cell Receptor Fragment Endowed with Antigen-Combining Properties", Proc. Natl. Acad. Sci. USA, 88:8646-8650 (1991).

Engel, et al., "High-Efficiency Expression and Solubilization of Functional T Cell Antigen Receptor Heterodimers", Science, 256:1318-1321 (1992).

Leiden and Strominger, "Generation of Diversity of the β Chain of the Human T-Lymphocyte Receptor for Antigen", Proc. Natl. Acad. Sci. USA, 83:4456-4460 (1986).

Jones, et al., "Partial Primary Structure of the Alpha and Beta Chains of Human Tumor T-Cell Receptors"Science, 227:311-314 (1985).

Leiden, et al., "Rearrangement and Expression of T-Cell Antigen Receptor Genes in Human T-Lymphocyte Tumor Lines and Normal Human T-Cell Clones: Evidence for Allelic Exclusion of Tiβ Gene Expression and Preferential Use of a Jβ2 Gene Segment", Mol. and Cell. Biol., 6:3207-3214 (1986).

Ferradini, et al., "Studies on the Human T Cell Receptor α/β Variable Region Genes", Eur. J. Immunol., 21:935-942 (1991).

```
  1  GGC GTA ACC CAA TCT CCG ACT CAC CTG ATC AAA ACG AGA GGA CAG
     CCG CAT TGG GTT AGA GGC TGA GTG GAC TAG TTT TGC TCT CCT GTC
  1  Gly Val Thr Gln Ser Pro Thr His Leu Ile Lys Thr Arg Gly Gln

46  CAC GTG ACT CTG AGA TGC TCT ATC TCT GGG CAC AAG AGT GTG
     GTG CAC TGA GAC TCT ACG AGA TAG GGA CCC GTG TTC TCA CAC
 16  His Val Thr Leu Arg Cys Ser Pro Ile Ser Gly His Lys Ser Val

91  TCC TGG TAC CAA CAG GTC CTG GGT CAG GGG CCC CAG TTT ATC TTT
     AGG ACC ATG GTT GTC CAG GAC CCA GTC CCC GGG GTC AAA TAG AAA
 31  Ser Trp Tyr Gln Gln Val Leu Gly Gln Gly Pro Gln Phe Ile Phe

136  CAG TAT TAT GAG AAA GAA GGA AGA GGA TTC CCT AAC TTC CCT GAT
     GTC ATA ATA CTC TTT CTT CCT TCT CCT AAG TTG AGA CTC GGA CTA
 46  Gln Tyr Tyr Glu Lys Glu Gly Arg Gly Phe Pro Asn Phe Pro Asp

181  CGA TTC TCA GCT CGC CAG TTC CCT AAC TAT AGC TCT GAG CTG AAT
     GCT AAG AGT CGA GCG GTC AAG GGA TTG ATA TCG AGA CTC GAC TTA
 61  Arg Phe Ser Ala Arg Gln Phe Pro Asn Tyr Ser Ser Glu Leu Asn

226  GTG AAC GCC TTG CTG GGG GAC CCC CTG TAT CTC TGT GCC
     CAC TTG CGG AAC GAC CTG AGC CGG GAC ATA GAG ACA CGG
 76  Val Asn Ala Leu Leu Gly Asp Ser Ala Leu Tyr Leu Cys Ala

271  AGC AGC   [SEQ ID NO. 25]
     TCG TCG   [SEQ ID NO. 26]
 91  Ser Ser   [SEQ ID NO. 27]
```

Fig. 1

T CELL ANTIGEN RECEPTOR V REGION PROTEINS AND METHODS OF PREPARATION THEREOF

INTRODUCTION

The present invention in the fields of immunology and medicine relates to expression vectors and methods for preparing commercially acceptable amounts of recombinant T cell antigen receptor V region proteins. Expression vectors are provided for the enhanced production of T cell antigen receptor V region proteins. The T cell antigen receptor V region proteins can be used in a variety of investigational, diagnostic and therapeutic settings. In a preferred aspect, the T cell antigen receptor V region proteins are used in treating or preventing an immune related disease.

BACKGROUND OF THE INVENTION

1. THE T CELL ANTIGEN RECEPTOR

The immune response to foreign antigens is divided into humoral immunity, mediated by B cells, and cellular immunity, mediated by T cells. The receptor molecules used by B cells to recognize antigen are immunoglobulins which recognize conformational epitopes on globular protein. The antigen receptors on T cells are related to immunoglobulins, but recognize processed antigen in association with self MHC molecules (Dembic et al., 1986, Immunol. Today 7:308).

TCR genes, like immunoglobulin genes, consist of regions which rearrange during T cell ontogeny (Chien et al., 1984, Nature 312:31–35; Hedrick et al., 1984, Nature 308:149–153; Yanagi et al., 1984, Nature 308:145–149). The human T cell receptor B chain locus has been extensively studied since the cloning of the first cDNA encoding the β-chain (Yanagi, Y., et al., 1984, Nature 308:145–149; Hedrick et al., 9184, Nature 308:149–152; Siu et al., 1984, Cell 37:393–401). This locus is a gene complex containing variable (V), diversity (D), and joining (J) gene segments which participate in somatic cell rearrangement with a constant (C) region gene segment to encode the β chain of the T cell receptor (Chien et al., 1984, Nature 309:322–326). By in situ hybridization, the TCRβ locus resides at 7q35 (Isobe et al., 1985, Science 228:580). By current estimates, this complex spans more than 600 kb and contains 70 to 80 variable region segments (Concannon et al., 1986, Proc. Natl. Acad. Sci. USA 83:6598–6602; Tillinghast et al., 1986, Science 233:879–883; Kimura et al., 1987, Eur. J. Immunol. 17:375–383; Lai et al., 1988, Nature 331:543–546). These V region genes are adjacent to two tandemly organized regions each of which include a D and a C gene segment separated by a cluster of six or seven J region gene segments (Tunnacliffe et al., 1985, Nucleic Acids Res. 13:6651–6661); Toyonaga et al., 1985, Proc. Natl. Acad. Sci. USA 82:8624–8628). Following successful DNA rearrangement of the V, D, and J gene segments, the translated β chain polypeptide pairs with a T cell receptor α chain and can be expressed on the surface of the T cell (reviewed by Kronenberg et al., 1986, Annu. Rev. Immunol. 4:529–591).

The TCR α and δ locus are next to one another on human chromosome 14. TCR δ coding segments are located entirely within the α gene locus (Satyanarayana et al., 1988, Proc. Natl. Acad. Sci. USA 85:8166–8170; Chien et al., 1987, Nature 330:722–727; Elliott et al., 1988, Nature 331:627–631). It is estimated that there are a minimum of 45–50 Vα regions (Becker et al., Nature 317:430–434) whereas there are only approximately 10 Vδ regions (Chien et al., 1987, supra). In peripheral blood, two predominant Vδ genes appear to be expressed, namely, Vδ 1 and Vδ 2.

The γ TCR gene was identified, first in mice (Saito et al., 1984, Nature 309:757–762; Kranz et al., 1985, Nature 313:762–755; Hayday et al., 1985, Cell 40:259–269) and then in humans (Lefranc et al., 1985, Nature 316:464–466; Murre et al., 1985, Nature 316:549–552). The human γTCR locus appears to consist of between five and ten variable, five joining, and two constant region genes (Dialynas et al., 1986, Proc. Natl. Acad. Sci. USA 83:2619).

TCR diversity, and thereby T cell specificity, is derived from several sources (Barth et al., 1985, Nature 316:517–523; Fink et al., 1986, Nature 321:219–225): the multiplicity of germline gene segments (Chien et al., 1984, Nature 309:322–326; Malissen et al., 1984, Cell 37:1101–1110; Gascoigne et al., 1984, Nature 310:387–391; Kavaler et al., 1984, Nature 310:421–423; Siu et al., 1984, Nature 311:344–349; Patten et al., 1984, Nature 312:40–46); combinatorial diversity through the assembly of different V, D, and J segments (Siu et al., 1984, Cell 37:393–401; Goverman et al., 1985, Cell 40:859–867); and junctional flexibility, N-region diversity and the use of either multiple D regions or any of the three translational reading frames for Dβ segments. TCR diversity does not appear to arise from the somatic hypermutation mechanism observed for immunoglobulins (Barth et al., supra). As a result of these mechanisms, TCRs are generated which differ in their amino-terminal, or N-terminal, domains (constructed from combinations of V, D, and J gene segments) but are similar elsewhere, including their carboxyl-terminal, or C-terminal domains (called constant regions). Accordingly, an extremely large repertoire of TCR is established.

Study of the structure and diversity of the human TCR β-chain variable region genes has led to the grouping of genes into distinct V region subfamilies (Tillinghast et al., 1986, Science 233:879–883; Concannon et al., 1986, Proc. Natl. Acad. Sci. USA 83:6598–6602; Borst et al., 1987, J. Immunol. 139:1952–1959). Each subfamily can be characterized by a consensus sequence and contains similar gene segments exhibiting greater than about 75% similarity in the DNA sequence. For instance, sixteen mouse Vβ sequences have been categorized into fourteen different subfamilies by a proposed arbitrary but simple numerical nomenclature for the V β gene segments (see Barth et al., 1985, "The Murine T Cell Receptor Employs a Limited Repertoire of Expressed Vβ Gene Segments" Nature 316:517–523). According to this nomenclature, members of the same subfamily share the first digit and differ in second; therefore the Vβ8.1, Vβ8.2 and Vβ8.3 are all members of the Vβ8 subfamily. A similar system has been proposed for the human gene segments. In humans, the approximately 60 functional Vβ genes have been grouped into at least 24 families (Toyonaga and Mak, (1988) Annu. Rev. Immunol. 5:585; Wilson et al., (1988) Immunol. Rev. 101:149; and Robinson, M. A. (1991) J. Immunol. 146:4392).

2. T CELLS IN AUTOIMMUNITY

T cells play a pivotal role in the differentiation and regulation of effector mechanisms within the immune system (Paul et al., 1987, Science 195:1293–1300). The co-recognition of antigen and major histocompatibility molecules by a T cell must be specific and precisely regulated, since improper immune regulation fosters autoimmunity.

Several laboratories have studied diseases in which there appears to be improper immune regulation, such as autoimmunity and some forms of immunodeficiency, and have implicated T cells in the pathogenesis of such diseases.

Several situations exist where there has been reported a clonal or oligoclonal expansion of a particular T cell receptor composition. The most obvious examples are in conditions of malignancy which have resulted in a T cell leukemia or lymphoma. (see for instance Jack et al., (1990) Am. J. Pathol. 136:17; Nitta, et al, (1990) Science 249:672; and, Yoshino et al., (1991) Int. J. Cancer, 47:654). In situations of T cell leukemias or lymphomas the T cell receptor acts as a unique tumor marker since the T cell receptor is stably rearranged and presented on the surface of the cell. Another situation where a particular T cell receptor composition is implicated is in the recipient of an organ graft whose T lymphocytes have T cell receptors making them aggressive against the MHC molecules of the donor individual, as for instance, the donor of a bone marrow graft.

Several groups have reported selective T cell antigen receptor V region gene usage in certain autoimmune situations. For instance, Grunwald et al, have noted a preferential expression of the V α 2.3 gene product in CD4+ T cells in the bronchoalveolar lavage when compared to peripheral blood lymphocytes of patients with Sarcoidosis (Grunwald, J. et al., (1992) Eur J. Immunol. 22:129). In Kawasaki disease the preferential expansion of Vβ 2 and Vβ 8 T cells was noted at the onset of disease (Abe, J., et al., (1992) Proc. Natl. Acad. Sci. U.S.A. 89:4066).

Rheumatoid arthritis has been extensively studied in this regard. Several investigators have noted preferential expansion of subsets of T cells, as for instance: DerSimonian, et al., (1993) J. Exp. Med. 177:1623 (preferential expansion of Vα 12.1 bearing T cells in CD8+ peripheral blood T lymphocytes); Stamenkovic, et al., (1988) Proc. Natl. Acad. Sci U.S.A. 85:1179 (synovial membrane-infiltrating T cells grown in IL2 were oligoclonal by southern blot analysis); Paliard, et al (1991) Science 253:325 (hypothesized that a superantigen activated Vβ 14+ T cells, including autoreactive T cells which expand clonally and migrate to the synovial fluid of rheumatoid arthritis patients); Howell et al., (1991) Proc. Natl. Acad. Sci. U.S.A., 88:10921 (noted in particular Vβ 3, 14, and 17 T cell V region gene usage in IL 2R+ cells from synovial fluid of rheumatoid arthritis patients); Uematsu, et al., Proc. Natl. Acad. Sci. U.S.A., 88:8534 (showed oligoclonal T cell V region gene usage in synovial fluid T cells of a single RA individual); International Publication No. 90/06758 (implicating Vβ 3, 9, and 10 in RA).

Inflammatory bowel disease has also been extensively studied. Several groups have noted expanded T cell population or preferential T cell receptor V region gene usage as for instance: Posnett et al, (1990) J. Clin. Invest. 85:1770; Spencer et al., (1991) J. Clin. Pathol. 44:915; Trejdosiewicz et al (1991) Clin. Exp. Immunol. 84:440; Van Kerckhove et al., (1992) J. Exp. Med., 175:57. Still others have reported preferential T cell V gene usage in Mycobacterium leprae (van Shooten et al., (1992) Proc. Natl. Acad. Sci. U.S.A., 89:11244; Wang et al., (1993) Proc. Natl. Acad. Sci. U.S.A. 90:188.

Multiple Sclerosis (MS) is an immune mediated disease characterized by central nervous system mononuclear cell infiltration and demyelination. Although the pathogenesis of MS is unknown, both genetic and environmental factors have been implicated in the disease process. Major elements of the genetic predisposition include an association of disease with particular class II major histocompatibility complex (MHC) haplotypes, in particular HLA-DR21 and DQw1 (Terasaid et al., Science (1976) 1933:1245–1247; Ho et al., (1982) Immunogenetics 15:509–517: Spielman et al., (1982) Epidemial. Rev. 4:45–65; Francis et al., (1986) Lancet 1:211; Elian et al., (1987) Disease Markers 5:89–99; Urban et al., (1988) Cell 54:577–592, Vandenbark, et al., (1989) Nature 341:541–544: Howell et al., (1989) Science 246:668–670.

It has been shown that T cells isolated from the cerebral spinal fluid of patients suffering from MS utilize a limited set of V region genes. The demonstration of in vivo activated myelin basic protein specific T cells in MS patients implicates MBP reactive T cells in the pathogenesis of the disease (Wucherpfennig, K. W., et al., (1990) Science 248:1016–1019). When the TCR Vβ usage of MBP reactive T cell lines is determined via polymerase chain reaction amplification of cDNA with T cell receptor Vβ primers, preferential usage of a limited number of Vβ genes has been found (Wucherpfennig, K. W., et al., 1990 supra (Vβ 17 and to a lesser extent Vβ 12 are frequently used in the recognition of the immunodominant region of the human autoantigen MBP); Oksenberg J. R., et al., 1993, Nature 362:68–70 (rearranged Vβ5.2 and/or Vβ5.3 genes were detected in the brains of patients with a certain HLA phenotype); Kotzin, B. L., (1991) Proc. Natl. Acad. Sci., 88:9161–9165 (a bias for use of the β chain variable region 5.2/5.3 and to a lesser extent Vβ 6.1 was seen among MBP specific clones from patients with MS). The results of some studies also imply that there is a limited T cell receptor V α gene expression in MS brain lesions (Oksenberg, J. R., et al., (1990) 345:344–346).

3. APPROACHES TO T CELL MEDIATED THERAPY

In the past efforts to selectively alter the T cell population of an individual have focussed on vaccination with either whole live or attenuated T lymphocytes (for a review of this approach see Cohen, I. R., Immunol. Rev. 94:5–21 (1986) or with peptide vaccines based on a specific portion of the T cell antigen receptor V region. The approach used by investigators takes advantage of the notion that potentially pathogenic T cells preferentially utilize a limited set of V region genes. The approach developed by Cohen uses live or attenuated T cells as a vaccination to treat or prevent, inter alia, experimental autoimmune encephalomyelitis (EAE). However, this approach is limited by the need to isolate clones of disease specific T cells. In this situation it is necessary to treat each patient with his own expanded cells, requiring "tailor-made" therapeutics (see, Zhang, et al., (1993) Science, 261:1451).

Others have suggested the therapeutic use of T cell receptor peptides based on the T cell V region gene involvement (Offner, H., (1991) Science 251:430 (Treatment with a peptide based on the T cell receptor Vβ8 amino acid sequence reduced severity of disease and speeded recovery in Lewis rats); Hashim, G. A., et al., (1992) J. Immunol. 149:2803–2809; Offner, H. et al., (1992) J. Immunol. 148:1706–1711; Offner, H., et al., (1991) J. Immunol., 146:4165–4172, but see Sun, D. (1992) Cell. Immunol. 141:200–210). These peptides are generally short peptides, usually between 8–25 amino acids in length, and rarely more than 30 amino acids in length. For example a 21 amino acid TCR peptide present on the TCR chain associated with EAE has been used to prevent EAE successfully in Lewis rats (Vandenbark A. A. et al., Nature 341:541–544 (1989);

Vandenbark, A. A., PCT Publication WO 91/01133 (7 Feb. 1991); see also, Janeway, C. A. Nature 341:482–483(1989)). Others have reported that even shorter peptides of 8 or 11 amino acids, corresponding to the β chain VDJ region or the Jα region proved effective as vaccines for either preventing or reducing the severity of EAE in a rat model (Howell, M. D. et al., Science 246:668–671 (1989); Howell, M. D. et al., PCT Publication WO 92/12996 (6 Aug. 1992)).

Peptides are commonly envisioned in this regard because of the ease of synthesis and because no method has been available until now for the production of useful quantities of T cell antigen receptor V region proteins. The major drawback of use of the small synthetic peptides is that they require that prediction be made about the particular sequence that would be effective in modulating an immune response. Predictions must be made as to the antigenic or immunogenic properties of the potential peptides, as for instance their occurrence in the CDR region of V region. Additionally, size of the peptide must be determined by considering the immunogenicity while maintaining the minimal epitope structure such that a T cell or an antibody specific for the peptide would recognize and react with the TCR on an intact T cell. This not only requires substantial time and experimentation, it is often impossible to predict efficacious peptide therapies in humans as the in vivo experimentation, which is required to ascertain the exact size and amino acid sequence, is not possible.

In addition, in order to obtain a specific antigenic response by a regulatory T cell, the peptide must be bound to the individuals' MHC molecules. These MHC antigens present on target cells have polymorphic regions wherein specific alleles are associated with particular individuals. For the most part, the individual will have two haplotypes, meaning that there will be two different alleles of a particular MHC antigen from the same locus. Not all peptides will have the capacity to bind to MHC antigens, nor will all MHC antigens bind to any single peptide, since there are multiple MHC antigens for each haplotype. Therefore, the suitability of such peptide approach to T cell mediated therapeutics must be determined on the haplotype of each individual, requiring tailor made peptides.

The present invention addresses these deficiencies and provides for the first time the successful production of a universal agent for a given T cell mediated disease for the treatment of an immune related disorder in which T cell subsets are implicated. The invention provides for a full length T cell antigen receptor V region protein that may be naturally processed, providing for multiple active fragments upon in vivo processing, and presented by antigen-presenting cells of each individual eliminating the need for "tailor-made" therapeutic agents.

4. PRODUCTION OF SOLUBLE T CELL ANTIGEN RECEPTOR

Production of large amounts of soluble T cell antigen receptor by recombinant techniques has been problematic for several reasons. A major obstacle to overcome in the production of soluble T cell antigen receptor is the secretion in the absence of the transmembrane region (Traunecker, A. et al. 1989 Immunol. Today, Vol. 10, pp 29–32). One investigator was able to show secretion of a full length monomeric β chain of the murine T cell antigen receptor including the V, D, and J regions followed by a truncated form of the Cβ region. The methodology took advantage of the homology between the carboxyl-terminal end of the immunoglobulin light chain and the sequence around Cys 241 in the TCR β chain. The resulting construct utilized the chimeric gene encoding the k-chain leader peptide sequence from MPC-11 and a rearranged VDJ exon. The resulting construct was expressed in mammalian cells and detectable in the cell supernatant. The method did not suggest however a means of obtaining a full length V region protein in the absence of extraneous protein sequences since secretion was dependant on presence of the truncated Cβ exon (Gasgoigne, N., (1990) J. Biol. Chem., 265(16):9296–9301).

Another group attempted to achieve the expression of a soluble form of the TCR β chain in biochemically significant quantities by the expression of a recombinant TCR heterodimer anchored by a phosphatidyl inositol glycan linkage. The method produced small (0.5 mg/harvest) amounts of a full TCR chain which necessitated the cleavage from the surface of the transfected cells by a phosphatidyl inositol specific phospholipase C (Lin, A. Y. Science (1990), 249:677–679).

Others have produced chimeric molecules by shuffling the variable and constant domains of murine T cell antigen receptors with the C region of an immunoglobulin κ light chain. The investigators were able to achieve small amounts of a secreted soluble form of a heterodimeric αβ T antigen receptor (Gregoire, C., et al., Proc. Natl. Acad. Sci. (1991), 88:8077–8081). Gregoire et al., show a murine chimera consisting of the Cα and Vα genes of the KB5-C2 joined to the C region of the κ light chain of the S105 monoclonal antibody. Also shown is a VβCβCκ chimera. Both are transfected into a mammalian B cell myeloma that does not express native immunoglobulin heavy or light chains. (see also, Weber, S., et al., (1992) Nature, 356:793–795).

Novotny et al., (1991) Proc., Natl. Acad Sci U.S.A. 88:8646–8650, demonstrate a method for producing soluble T cell antigen receptors with antigen combining properties. A synthetic oligo linker was cloned onto the C terminus of the Vβ and the N terminus of the Vα region resulting in a single chain VβVα. The resultant expression vector encodes the pelB leader followed immediately by in frame Vβ, the linker, and the Vα segments. The expression of this construct is under the control of the lacZ promoter and is therefore IPTG inducible.

Recently, one group has shown the secretion of a small amount of a T cell receptor V region fused to a carboxyl-terminal Histidine tail. The plasmids contain the pelB leader and are under the control of chemically inducible promoter (Ward, E. S., (1991) Scand. J. Immunol., 34:215–220). The work fails, however to describe how to obtain a T cell antigen receptor V region in the absence of a fusion partner, nor how to obtain commercially feasible amounts of the receptor V region.

There is a great need, therefore, for agents and pharmaceutical compositions which have the properties of specificity for the targeted autoimmune response, predictability in their selection, and convenience and reproducibility of preparation.

SUMMARY OF THE INVENTION

In accordance with the primary objective of this invention a method of producing a recombinant T cell antigen receptor V region protein is provided. Also provided are a class of recombinant expression vectors for the expression of T cell antigen receptor V region proteins in bacteria. The recombinant T cell antigen receptor V region proteins of the instant invention are useful in the treatment, prevention or suppression of an immune related disorder. In another embodiment the T cell antigen receptor molecules can be combined in an admixture with a pharmaceutically acceptable carrier for use as a therapeutic composition. In another embodiment the claimed T cell antigen receptor V region proteins are useful to generate anti-receptor antibodies. Alternatively, the T cell antigen receptor V region proteins can be used diagnostically to characterize a particular immune related disorder. In another embodiment the T cell antigen receptor V region proteins of the instant invention can be used as diagnostic probes based upon the ability of the soluble T cell antigen receptor V regions to detect autoantibodies. It is an advantage of the present invention that the T cell antigen receptor V region proteins are expressed in the absence of fusion proteins or affinity tails. It is a further advantage of the present invention that the T cell antigen receptor V region proteins are produced in biologically significant amounts.

In one embodiment the invention provides for an expression vector for the production of a pure T cell antigen receptor molecule. The expression vectors of the invention include as an essential element, a T cell antigen receptor V region gene. The T cell antigen receptor gene of the invention is any full length T cell antigen receptor gene. In a preferred aspect, the T cell antigen receptor gene encodes the Vβ5.3 variable region of the T cell antigen receptor.

The expression vectors provide in the broadest embodiment for the inducible regulation of the T cell antigen receptor V region protein. In a preferred embodiment the T cell antigen receptor V region gene is under the transcriptional control of an inducible bacterial promoter. According to the present invention the inducible bacterial promoter is subject to either chemical or thermal regulation. In a preferred embodiment the inducible bacterial promoter is subject to thermal induction.

In one embodiment the expression vector of the instant invention includes a regulatory gene coding for a protein capable of binding to the promoter and thereby repressing transcription from the inducible promoter. In a preferred embodiment the promoter is derived from the E. coli lac gene and the regulatory gene comprises a functional mutation of the E. coli lacI gene. In one aspect the mutation of the lacI gene causes the temperature sensitive inducibility of the promoter. In a preferred embodiment the inducible bacterial promoter is a trc promoter and the thermal induction is provided by the lacIts regulatory gene.

In one embodiment the regulatory gene is located on a cotransformed vector. In another embodiment the regulatory gene is located in the bacterial host cell chromosome. In a preferred embodiment the regulatory gene is located in the recombinant expression vector. In a further preferred embodiment the transcription direction of the intact functional mutation of the lacI gene is in the same orientation as the T cell antigen receptor structural gene to be expressed.

The present invention provides for two subclasses of recombinant expression vectors. The members of the one class of plasmids contain a leader sequence. The members of the second class do not contain a leader sequence. The particular plasmid selection can influence the choice of bacterial host strains to be transformed. The bacterial expression vectors of the present invention which do not contain a leader sequence facilitate the expression of the T cell antigen receptor protein in protease deficient bacterial strains. On the other hand, the bacterial expression vectors of the present invention which do contain a leader sequence facilitate expression in other bacterial strains.

In yet another preferred embodiment the recombinant expression vectors of the present invention comprise in the 5' to 3' direction; a trc promoter, a ribosome binding site, an optional leader sequence, a T cell antigen receptor V region gene, a stop codon, a transcription terminator, a lacIts regulatory gene such that the transcription direction is the same as that of the T cell antigen receptor V region to be transcribed, a bacterial origin of replication, and a tetracycline resistance gene.

Also in accordance with the primary objective of the invention a method has been developed which allows for the production of enhanced levels of gene expression and protein expression of the T cell antigen receptor V region. According to the method of expression, the preferred expression vectors of the invention are introduced into a suitable bacterial host cell. In one embodiment the bacterial host cell, a cotransformed vector, or the expression vectors of the instant invention, contain a gene for a thermolabile repressor. Increasing the temperature of the system to a temperature at which the repressor is inactivated renders the host cell capable of effecting expression of the T cell antigen receptor V region gene.

In yet another embodiment the present invention provides for treating a subject with an immune related disorder. Such treatment comprises administering to a subject in need of such treatment, a pharmaceutical composition in accordance with the present invention, in an amount and for a period of time suitable to regulate said immune disorder. It is an advantage of the present invention that the compositions of the invention allow for treatment of an immune related disorder without the need to select a particular peptide fragment or tailoring the particular composition to the particular individual to be treated. The invention therefore allows for ease of treatment as well as broad spectrum treatment.

The invention also relates to the use of a full length T cell antigen receptor V region protein in therapy. In a specific embodiment the invention relates to the use of a full length Vβ5.3 protein in therapy. In another embodiment the invention provides for the use of a full length T cell antigen receptor V region protein in the manufacture of a medicament. Therefore in one embodiment the invention provides the use of a Vβ5.3 protein in the manufacture of a medicament. In a further embodiment the invention relates to the use of a full length T cell antigen receptor V region protein and especially Vβ5.3 in the manufacture of a medicament for the treatment of an immune related disease or disorder. In a specific preferred embodiment the full length T cell antigen receptor V region protein is Vβ5.3 and the immune related disease or disorder is multiple sclerosis.

BRIEF DESCRIPTION OF THE FIGURES

FIG. 1. The complete nucleotide sequence [SEQ ID NO. 25 and SEQ ID NO. 26] and amino acid sequence [SEQ ID NO. 27] of the full length Vβ5.3 protein of the invention.

DETAILED DESCRIPTION OF THE INVENTION

Figure 2:
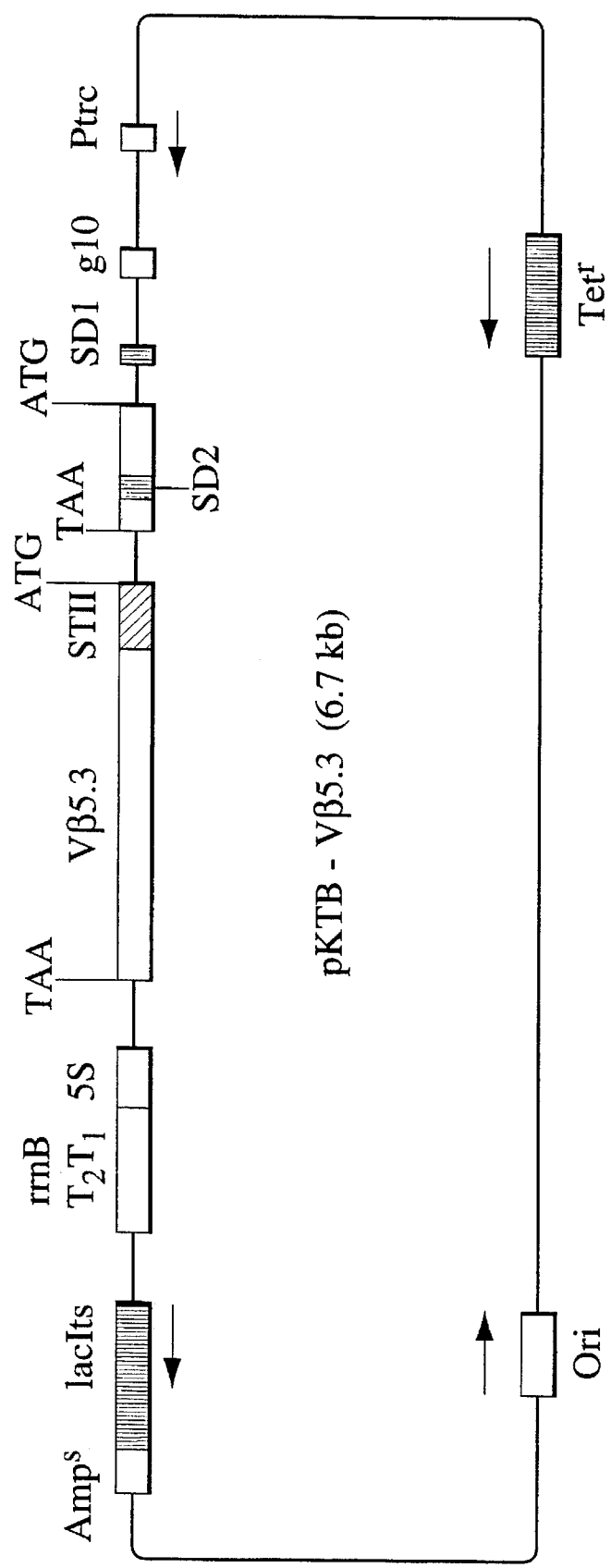
FIG. 2. Plasmid pKTB-Vβ5.3. This plasmid contains Ptrc; the trc promoter; g10, g10 leader gene segment from bacteriophage T7; SD1, ribosome binding site; MC, minicistron coding for 8 amino acid residues, upstream of the STII leader, and containing a second ribosome binding site; STII, the STII leader sequence; Vβ5.3, the Vβ5.3 gene; T1T2, transcription terminators; the lacIts gene encoding the temperature sensitive lac repressor; Ori, the origin of replication and Tet$^r$, the tetracycline resistance gene.

The present invention describes recombinant expression vectors and methods for the efficient production of large quantities of a T cell antigen receptor V region protein and the use thereof in several situations including the treatment, prevention or suppression of immune related diseases.

A series of vectors have been developed for the achievement of enhanced levels of expression of a full length T cell antigen receptor V region gene. Additionally, a method is provided for producing commercially feasible amounts of a full length recombinant T cell antigen receptor V region protein using the expression vector of the instant invention. The methods and expression vectors of the instant invention are unique because they provide for the production of a full length T cell antigen receptor V region in the absence of extraneous protein sequences or fusion partners. As detailed in the Background of the Invention, supra, T cell antigen receptor V regions have, in the past, only been produced as part of a larger protein. The usual scenario provides for a V region protein in association with extraneous proteins which enhance production and/or handling of the protein. These other proteins can cause undesirable immunogenicity and present regulatory and safety concerns. In the past the V region protein includes other regions of the T cell antigen receptor, such as the constant region, fused to the V region. Others have constructed expression systems that provide for a T cell antigen receptor V region as a chimeric protein. The usual chimeric protein provides for a V region fused to portion of an immunoglobulin molecule. Still others have provided the T cell antigen receptor as part of a fusion protein. The present invention therefore provides for the production of a T cell antigen receptor V region protein in the absence of extraneous protein sequences or fusion partners.

The expression vectors and methods of the instant invention further provide for enhanced levels of expression of a T cell antigen receptor V region protein. A primary consideration in the production of a protein that has commercial utility, for example, in the field of research and diagnostics and therapeutics, is the manufacture of commercially feasible amounts of a protein. The present invention therefore provides for the production of enhanced levels of T cell antigen receptor V region proteins. The level of production of the T cell antigen receptor V region protein of the instant invention is usually between 1 and 100 mg/liter of culture supernatant. In preferred aspects the production level of the T cell antigen receptor is between 10 and 50 mg/liter. In a more preferred embodiment, the methods of the instant invention provide for the production of 0.5 mg/milliliter of culture supernatant.

The methods and expression vectors of the instant invention further provide for the efficient production of a T cell antigen receptor V region production. The methods and expression vectors of the instant invention provide for the production of a T cell antigen receptor V region protein in the absence of extraneous protein sequences. The invention therefore eliminates several steps associated with obtaining a purified T cell antigen receptor V region protein. In one embodiment therefore, the invention provides for the thermal induction of the protein expression. Hence the invention provides for a relatively pure T cell antigen receptor V region in the absence of chemical inducers.

As noted above the invention provides for the T cell antigen receptor V region in the absence of extraneous proteins. The invention therefore provides for simplified production of a relatively pure T cell antigen receptor V region. Therefore, in a preferred aspect, the invention eliminates additional steps in purification of a T cell antigen receptor V region such as the need to introduce enzyme or chemical reagents into the system, such as those required to obtain a protein free of any fused affinity tails.

1. T CELL ANTIGEN RECEPTOR V REGION

The T cell antigen receptor V region protein of the instant invention is any full length T cell antigen receptor V region. A full length T cell antigen receptor V region is encoded by a T cell antigen receptor V region gene. V region, within the scope of the present invention includes the variable region of the T cell antigen receptor. In its broadest aspect this region includes the joining and diversity regions. The T cell antigen receptor V region gene of the invention provides for the production of T cell V region protein in the absence of extraneous coding sequences. The T cell antigen receptor V region gene of the invention is therefore limited to a nucleotide sequence encoding a full length T cell antigen receptor V region protein. Such a protein is produced in the absence of extraneous protein sequences such as, for instance, other T cell antigen receptor regions, such as the constant region or the transmembrane region or the cytoplasmic region. Further, the T cell antigen receptor V region protein of the invention is produced in the absence of fusion proteins such as affinity tails. Further, the T cell antigen receptor V region protein of the invention is not produced as a part of a larger chimeric protein including portions of other protein molecules such as an immunoglobulin protein.

The full length T cell antigen receptor V region protein of the present invention can be any of the T cell antigen receptor V region. Therefore the T cell antigen receptor V region protein can be a variable region of the α subunit, the γ subunit, the δ subunit, or the γ subunit.

In a preferred embodiment the T cell antigen receptor V region protein of the instant invention is any T cell antigen receptor V region for which a full length coding sequence is available. Methods of obtaining the full length coding sequences of the instant invention are well known in the art. Human V region domain DNA sequences can be isolated in accordance with well known procedures from a variety of human cells. Preferably the cells are peripheral blood T lymphocytes.

The DNA sequences of the present invention may be prepared in various ways. It is preferred that the DNA sequences of the T cell antigen receptor V regions be prepared by polymerase chain reaction (PCR) using DNA sequences coding for the intact T cell antigen receptor as templates. A human Vβ region can be prepared, for instance, via amplification of cDNA prepared from human peripheral blood lymphocytes stimulated by an anti-CD3 antibody, following the procedure of Choi et al., (1989) Proc. Natl. Acad. Sci. 86:8941–8945.

In one aspect of the present invention the full length T cell antigen receptor V region gene is obtained from any clone containing the full length sequence. For a non-limiting description of the T cell antigen receptor V region sequences and cDNA clones containing the full length sequence see for instance, Concannon et al., (1986) Proc. Natl. Acad. Sci. U.S.A. 83:6598–6602.

In a preferred embodiment the T cell antigen receptor V region of the instant invention is any T cell antigen receptor V region that is implicated in an immune related disease or disorder. Specific non-limiting examples of the T cell antigen receptor V region genes of the invention include Vβ 8.1 (Kawasaki disease; see, Abe et al., (1992) Proc. Natl. Acad. Sci. U.S.A. 89:4066), Vβ 6.1 (leprosy; see, Wang, et al., (1993) Proc. Natl. Acad. Sci. U.S.A., 90:188), Vβ 5.1 (Lyme disease; see Lahesma et al., (1993) J. Immunol. 150:4125), Vβ 5.2, or Vβ5.3, or Vβ 6.1 (multiple sclerosis; see Kotzin, et al., (1991) Proc. Natl. Acad. Sci. U.S.A. 88:9161), Vβ 2.1, or Vβ 3.1 (rheumatoid arthritis; see Uematsu, et al., (1991)

Proc. Natl. Acad. Sci. U.S.A. 88:8534). Therefore, in preferred embodiments the T cell antigen receptor of the invention is any T cell antigen receptor V region that characterizes the T cell antigen receptor on T lymphocytes implicated in certain autoimmune etiologies. In another embodiment the T cell antigen receptor V region protein is any T cell antigen receptor V region protein for which there is an increased gene expression. (Hafler, D. A. et al., J. Exp. Med. 167:1313 (1988); Mantgazza R. et. al., Autoimmunity 3:431 (1990)).

The TCR expressed by a T cell clone in an autoimmune disease or a T cell clone responding to a particular autoantigen can be identified using TCR-specific antibodies, either polyclonal, monoclonal or chimeric which are specific for a TCR variable segment to detect surface expression, employing techniques of fluorescence microscopy, flow cytometry, immunocytochemistry, or other techniques known in the art. Such antibodies have been described for a number of TCR α and/or β chain V regions (see, for example, Internation Publication No. Wo 90/06758).

Alternatively, the DNA or mRNA of the T cell clone can be probed directly, or after amplification by the polymerase chain reaction (Synha et al., Science 239:1026(1988); Saiki et al., Nature 324:163 (1986), by specific hybridization with nucleic acid probes for the various TCR gene families, using hybridization methods well known in the art. The TCR sequence, or a part thereof, can then be obtained directly from the amplified, rearranged DNA or mRNA.

Expression of a particular TCR can also be identified by determining the nucleic acid sequence encoding at least part of the TCR, for example, after cloning the TCR V gene, or by determining the amino acid sequence of at least part of a TCR protein. It will be apparent that any of the above-mentioned approaches, or additional approaches known to one of skill in the art, will result in the identification of the TCR expressed on a T cell or clone or line of T cells.

Non-limited examples of molecular approaches used to correlate TCR gene expression with disease include:

(1) producing and analyzing cDNA libraries obtained from the disease-related T cells obtained from one or more subjects having the disease, to determine the presence of frequently used or 'dominant' TCR genes;

(2) Southern analysis of disease samples to determine whether specific genetic polymorphism (e.g., RFLPs) or oligoclonal TCR rearrangements exist;

(3) analysis of disease samples by cDNA synthesis, PCR amplification, and slot blot hybridization procedures;

(4) in situ nucleic acid hybridization of TCR probes to T cells without prior culture of these cells.

In a preferred embodiment the full length T cell antigen receptor V region protein is the Vβ 8.1, Vβ 5.2, or Vβ5.3 V region. In a more preferred embodiment the T cell antigen receptor V region protein is the Vβ5.3 region. Therefore, in one embodiment the T cell antigen receptor V region of the instant invention is encoded by a gene which encodes for the Vβ5.3 V region. In a preferred embodiment the gene contained in the expression vector of the instant invention encodes the human T cell antigen receptor Vβ5.3. In particular the gene encoding the T cell antigen receptor V region protein of the instant invention has the sequence shown in FIG. 1.

A T cell antigen receptor V region clone can be introduced into the expression vectors of the instant invention by methods known to those of skill in the art. From the cDNA clone, the V region is PCR synthesized incorporating an initiating methionine at the 5' terminus. Any convenient restriction site can be synthesized which incorporates an initiating methionine and reconstitutes the 5' coding region of the V gene. In a preferred embodiment, the restriction site is the NcoI site. An appropriate restriction site is engineered at the 3' end of the V region coding sequence so that it can be subcloned into the polylinker contained in the expression vector.

It should be understood that the methodology of the present invention can be used to prepare soluble full length T cell antigen receptor V region derived from animal species other than human.

2. EXPRESSION VECTORS

A recombinant expression vector within the scope of the present invention is a plasmid which contains exogenous DNA in the form of the T cell antigen receptor V region gene to be expressed. The recombinant expression vector of the present invention is inserted into a bacterial host cell by transformation and transformants are isolated and cloned, with the object of obtaining large amounts of the desired V region protein.

The present invention concerns expression vectors containing the DNA sequence coding for the full length T cell antigen receptor V region protein. Preferably the T cell receptor V region proteins are those T cell antigen receptor proteins described herein. An expression vector within the scope of the present invention is a plasmid which contains the T cell antigen receptor V region gene to be expressed under the transcriptional and translational control of regulatory elements as for instance the promoter, ribosomal binding site and transcription terminator. In addition it contains an origin of replication for stable replication in bacteria. In also includes a gene coding for resistance to an antibiotic to facilitate selection of plasmid bearing cells. Expression of the cloned sequence occurs when the expression vector is introduced into an appropriate host cell.

Expression vectors useful in the present invention are often in the form of plasmids. Plasmids refer to circular double stranded DNA sequences which in their vector form, are not integrated in the chromosome. The expression vectors of the present invention may also include other DNA sequences known in the art, for example leader or signal sequences which provide for targeting or stability of the expression product, regulatory sequences which allow expression of the structural gene to be modulated, as for example by a shift in temperature or a change in composition of the growth medium.

In a preferred embodiment, the expression vectors contain one or more control sequences operably linked to the DNA sequences coding for the soluble TCR V region. The DNA sequence within the control region of the gene which mediates the initiation of transcription is termed the promoter of the gene. The term operably linked within the scope of the present invention means that a genetic sequence is operationally linked to nucleic acid segments or sequences either upstream or downstream from a given segment. Those nearby segments typically affect processing or expression of the specified nucleic acid sequence. As used in this context, the term operably linked means that the control DNA sequences are capable of directing the expression of the DNA coding for the full length TCR V region.

In one embodiment the promoter, which directs the synthesis of the RNA encoding the T cell antigen receptor V region protein may be any inducible promoter. In a preferred embodiment the promoter is one that is regulated by the presence or absence of certain media components. One skilled in the art will recognize that several bacterial promoters subject to the control of the presence or absence of certain media components can be used in connection with the expression vectors of the instant invention. It is preferred that the promoter be a strong bacterial promoter such as the lac promoter, the tac promoter, and the trc promoter. Therefore in one embodiment the promoter is subject to regulation by presence or absence of isopropyl-β-D-thiogalactopyranoside (IPTG). In preferred aspects the promoter is the lac promoter or the tac promoter. In a preferred embodiment the promoter is the trc promoter (Brosius et al. (1985) J. Biol. Chem. 260:3539–3541) which is similar to the tac promotor derived by fusing the −10 region of the lac UV5 promoter with the −35 region of the tryptophan promoter (de Boer et al. (1983), Proc. Natl. Acad. Sci. USA 80:21–25; Amann et al. (1983) Gene 25:167–178.) The trc promoter is identical to the tac promoter with the exception of 1 bp change in the promoter (Brosius et al., (1985) supra).

In a further embodiment the expression vector of the instant invention is modified to allow for the secreted expression of the full length T cell antigen receptor V region protein of the invention by a shift in the temperature. Therefore in a preferred embodiment the expression vector allows for the expression of TCR V region protein in the absence of chemical inducers. According to the present invention this obviates the need to use IPTG and bacterial strains containing the lacI or the lacIq genes. Therefore, one embodiment of the expression vector of the instant invention includes a regulatory gene which allows for the thermal induction of the protein expression. In a preferred embodiment the regulatory gene sequence encodes the temperature sensitive lac repressor. In a preferred embodiment the regulatory gene sequence is the lacIts gene encoding for a temperature sensitive lac repressor.

In a further preferred embodiment the gene encoding for the temperature sensitive lac repressor molecule is located proximal to and downstream of the transcription terminator and its transcription direction is the same as that of the V region coding sequence.

In addition the plasmid contains the tetracycline resistance gene. It will be recognized by one of skill in the art that genes which encode a variety of selectable markers may be used in conjunction with the plasmid of the invention. In a preferred embodiment the selectable gene confers resistance to a drug such as ampicillin, kanamycin or tetracycline. In a more preferred embodiment the selectable marker is the tetracycline resistance gene.

Additionally, the vector includes a bacterial origin of replication. In a preferred embodiment the origin of replication is derived from pBR322. The expression vector also contains a ribosome binding site and the transcription terminators of the rrnB ribosomal RNA operon of *E. coli* (Brosius et al. (1981), Plasmid 6:112–118.)

In a preferred embodiment the expression vector of the instant invention contains as essential elements in the 5' to 3' direction a DNA sequence which contains a promoter and an operator; a DNA sequence which contains a ribosomal binding site for rendering the mRNA of the desired gene capable of binding to ribosomes within the host cell; an ATG initiation codon or a DNA sequence which is converted into an ATG initiation codon upon insertion of the desired gene into the vector; a restriction site for the insertion of the desired gene in phase with the ATG initiation codon or a multiple cloning site containing several restriction sites for the insertion of the appropriate gene to be expressed; the T cell antigen receptor V region gene to be expressed; a transcription terminator which serves to efficiently terminate transcription. The vector also contains a DNA sequence which contains an origin of replication from a bacterial plasmid capable of autonomous replication in the host cell and a DNA sequence which contains a gene associated with a selectable or identifiable phenotypic trait which is manifested when the vector is present in the host. The expression vector may optionally include a signal or leader sequence fused to the 5' end of the TCR V region gene to be expressed. In certain preferred embodiments the expression vector contains a regulatory gene which allows for the expression of the secreted protein by a temperature shift.

In a preferred embodiment the expression vector contains the following essential elements in 5' to 3' direction: The trc promoter which is composed of the −10 region of the lac UV5 promoter fused with the −35 region of the tryptophan promoter (de Boer et al., supra; Amann et al. (1983) supra); a strong ribosome binding site; the T cell antigen receptor V region gene to be expressed; the transcription terminators from the rrnB operon; the lacIts gene coding for the temperature sensitive lac repressor; the pBR322 origin of replication; and a tetracycline resistance gene. In a preferred embodiment the expression vector is pKBi-Vβ5.3

In one embodiment the expression vector contains a leader sequence. The leader sequence could encode any amino acid sequence which, when expressed as an amino terminal peptide, and linked to the T cell antigen receptor structural gene, is capable of directing the secretion of the heterologous protein into the periplasm or the culture medium. One skilled in the art will recognize that many leader sequences may be used in connection with the expression vector of the instant invention. In a preferred embodiment the leader sequence is the pelB signal sequence from *E. carotovora* (Lei et al. (1987), J. Bacteriology 169:4379–4383). In another preferred embodiment, the leader sequence is the heat stable enterotoxin II(STII) signal sequence of *E. coli* (Morioka-Fujimoto et al. (1991) J. Biol. Chem. 266:1728–1732).

In one embodiment the expression system contains the STII leader sequence and the V region structural gene is PCR synthesized to contain an appropriate restriction site at the 3' end and an engineered MluI site at the 5' end so that it can conveniently link to the MluI site incorporated into the 3' end of the STII leader.

Therefore in a further preferred embodiment, the expression vector is the vector containing in the 5' to the 3' direction; the trc promoter which is composed of the −10 region of the lac UV5 promoter fused with the −35 region of the tryptophan promoter (de Boer et al., supra); a strong ribosome binding site; the STII leader; the T cell antigen receptor V region gene to be expressed; the transcription terminators from the rrnB operon; the lacIts gene coding for the temperature sensitive lac repressor; the pBR322 origin of replication; and a tetracycline resistance gene. In a most preferred embodiment the expression vector is pKB-Vβ5.3.

The expression vectors of the present invention may be constructed using standard techniques known in the art, many of which are described in Maniatis et al., *Molecular Cloning: A Laboratory Manual,* Cold Spring Harbor Laboratory, Cold Spring Harbor, N.Y. (1982).

The present invention additionally concerns host cells containing an expression vector which contains a DNA sequence coding for a soluble full length T cell antigen receptor V region. Additionally, preferred host cells contain an expression vector comprising one or more control DNA sequences capable of directing the replication and or the expression of a DNA sequence coding for a soluble full length T cell antigen receptor V region. Suitable host cells include prokaryotic host cells. In preferred aspects the prokaryotic host cell is a bacterial host cell such as an *E. coli* cell.

One skilled in the art will understand from the teaching of the instant application that the particular expression vector used will influence the choice of host strains selected for the production of the full length T cell antigen receptor V region protein. For instance, in the expression vectors subject to chemical induction within the scope of the present invention, bacterial host strains which harbor the lacI or lacIq gene which regulate the trc promoter are especially useful. In expression vectors within the scope of the present invention that contain a regulatory gene such as the lacIts gene which provides for a temperature sensitive repressor, bacterial host strains that do not harbor the wild type lacI or lacI$^q$ genes are preferred. A particularly preferred host cell is LJ24.

In certain embodiments the expression vector of the instant invention does not contain the leader sequence. Therefore, in certain embodiments the choice of vector constructs will affect the choice of bacterial host strains. In certain preferred embodiments the bacterial host strain is BL21, SG21163, SG22094, or SG21173 bacterial host strain.

The expression vectors of the present invention may be introduced into the host cells by various methods known in the art which may vary depending on the type of cellular host. For example, calcium chloride treatment or electroporation are commonly utilized for prokaryotic cells (See, generally, Maniatis, et al., 1982, *Molecular Cloning: A Laboratory Manual*, Cold Spring Harbor Press).

Once the expression vector has been introduced into an appropriate host cell, the host cell may be cultured under conditions permitting expression of large amounts of soluble T cell antigen receptor V region.

Host cells containing an expression vector which contains a DNA sequence coding for a soluble T cell antigen receptor V region may be identified by one or more approaches as for instance detection of the gene product immunologically, as for instance in an immunoassay such as those described in the Example sections.

Alternatively the host cell containing the expression vector of the instant invention may be identified by assessing the level of transcription as measured by the production of mRNA transcripts in the host cell. In yet another embodiment the host cell containing the expression vectors of the instant invention can be identified by DNA-DNA hybridization using probes complementary to the DNA sequence.

The DNA sequences of the present invention, expression vectors or DNA molecules may be determined by various methods known in the art. For example the dideoxy chain termination method as described in Sanger et al., (1977) Proc. Natl. Acad. Sci. U.S.A. 74:5463–5467.

It should be noted that not all expression vectors and DNA sequences will function equally well to express the DNA sequences of the present invention. However, one skilled in the art may make a selection among expression vectors, DNA sequences, and host cells using the guidance provided herein without undue experimentation and without departing from the scope of the present invention.

Once expressed, the proteins of the present invention can be purified according to standard procedures of the art, including ammonium sulfate precipitation, affinity columns, column chromatography, gel electrophoresis and the like (see. generally, Scopes, R., 1982, *Protein Purification*, Springer-Verlag, N.Y.).

The cloning vehicles of the instant invention are useful to make available for the first time and to increase the supply of the gene encoding the T cell antigen receptor. With this abundance of the desired gene product the means necessary to make proteins available at a lower cost is available.

In a preferred embodiment, the T cell antigen receptor V region is soluble. By this it is meant that the T cell antigen receptor V region is soluble in an aqueous system. A "soluble" protein is generally characterized by its failure to sediment at room temperature under high G-force centrifugation (100K) out of an aqueous buffer. Solubility is particularly important in providing simplicity in purification of the T cell antigen receptor V region protein from the producing cell. Aqueous buffers used in protein chemistry typically have a buffering compound for providing a pH, typically within a physiological rate of about 5–9, an ionic strength typically between about 10 mM and about 500 mM, often a protease inhibitor and a mild detergent. Examples of standard buffers are phosphate buffered saline, tris-buffered saline or any of a number of buffers used in protein isolation. See generally, volumes of Methods in Enzymology; Mahler and Cordes (1966) *Biological Chemistry* (2d Ed.) Harper and Row, New York.

3. USE OF T CELL ANTIGEN RECEPTOR V REGION PROTEINS

A. Diagnostic, therapeutic and investigational use

The present invention provides for the first time the means for efficiently and economically producing diagnostic, therapeutic and investigationally useful quantities of a T cell antigen receptor V region protein. By providing means for producing large amounts of a soluble T cell antigen receptor V region protein, a molecule which is heretofore not available in a form that is not a fusion protein nor linked to an affinity tail, the present invention provides several distinct advantages and uses.

In one embodiment the present invention provides for recombinant expression vectors that are useful in producing large quantities of T cell antigen receptor V region protein. The invention is significant because it provides both the expression system and the process for producing a quantity of pure T cell antigen receptor V region proteins that are not fusion proteins and are not linked to affinity tails.

The T cell antigen receptor V region proteins of the instant invention provide advantages over the presently available molecules because they eliminate the need for post production processing of the proteins. The T cell antigen receptor V region proteins do not require that, for instance, the affinity tail be cleaved prior to use. This presents the advantage in that there is no need to introduce extraneous chemical or enzymatic entities to the resulting product. Manufacturing large amounts of a protein for which one intended use may be the therapeutic administration of the protein the need for a pure product is tantamount. As will be understood by one of skill in the art the elimination of post production manipulation addresses regulatory concerns as well as concerns of efficiency and cost of production. Furthermore, the present invention provides for reduced production costs and overall ease in handling.

B. Investigational use and diagnostic use

The T cell antigen receptor V region proteins of the present invention, once produced can be used in a variety of settings. In one embodiment the present proteins are useful in an investigational setting. The T cell receptor proteins of the invention are also useful in structural and functional studies on the T cell receptor. Besides serving as substrates or binding domains for specific forms of T cell receptors, these proteins may serve as tools for the investigation of conformational studies to approximate the native configurations of various portions of the T cell receptor. In yet another embodiment, the T cell proteins can be used as diagnostic probes. In one specific embodiment, the T cell antigen receptor V region proteins of the present invention may be used in determining the amount or the presence of a certain T cell V region subfamily in a biological sample. One such assay is described in Rittershaus C. W., PCT Publication WO92/08981, published May 26, 1992 entitled "Therapeutic and Diagnostic Methods Using Total Leukocyte Surface Antigens". As such the present invention provides for methods for diagnosing an immune related disease, such as multiple sclerosis (MS), based on detecting the specific subset of T cell antigen receptor in a biological sample.

In another embodiment the present invention can be used in the generation of significant quantities of T cell antigen receptor V region proteins for use in antibody production. The antibodies can be prepared by using any of a number of techniques well known in the art. For producing a mAb, any method which provides for the production of antibody molecules by continuous cell lines in culture may be used, for example. These methods include, but are not limited to the hybridoma techniques originally described by Kohler and Milstein (1975), Nature, 256:495–497), and the more recent human B cell hybridoma technique (Kozbor et al., 1983. Immunology Today, 4:72) the EBV technique (Cole et al., 1985, "Monoclonal Antibodies and Cancer therapy", Alan R. Liss, Inc., pp. 77–96, and trauma techniques. For a review of antibody production methods see: Hartlaw, E., et al., "Antibodies: A laboratory Manual", Cold Spring Harbor Laboratory Press, Cold Spring Harbor, N.Y., 1988.

In yet another diagnostic embodiment the T cell antigen receptor V region protein of the invention can be used as a diagnostic probe based on the ability of the soluble T cell antigen receptor V region protein to detect the presence of autoantibodies.

The present invention also contemplates derivatives of the T cell antigen receptor V region proteins. Such derivatives include, for example $^{125}$I, $^{131}$I, $^{14}$C, $^{35}$S, $^{3}$H, $^{112}$In, $^{99}$M, Tc and the like, for in vitro and in vivo diagnostic purposes.

C. Therapeutic use

As mentioned above, the present invention is useful in the therapy of immune-related disease. The term "immune-related disease" as used herein refers to a disease in which the immune system is involved in the pathogenesis of the disease, or in which appropriate stimulation of the immune system can result in protection from the disease. Relevant diseases include, but are not limited to, autoimmune diseases, neoplastic diseases, infectious diseases, hypersensitivity, transplantation, graft-versus-host disease, and degenerative nervous system diseases. Autoimmune diseases include, but are not limited to, arthritis, such as rheumatoid arthritis, type I diabetes, juvenile diabetes, multiple sclerosis, autoimmune thyroiditis (Hashimoto's thyroiditis), myasthenia gravis, systemic lupus erythematosus (SLE), Sj ögren's syndrome, Grave's disease, Addison's disease, Goodpasture's syndrome, scleroderma, dermatomyositis, myxedema, polymyositis, pernicious anemia, inflammatory bowel disease including Crohn's disease and autoimmune atrophic gastritis, and autoimmune hemolytic anemia. Neoplastic diseases include, but are not limited to, lymphoproliferative diseases such as leukemias, lymphomas, Non-Hodgkin's lymphoma, and Hodgkin's lymphoma, and cancers such as cancer of the breast, colon, lung, liver, pancreas, melanoma, renal carcinoma, etc. Infectious diseases include but are not limited to viral infections caused by viruses such as HIV, HSV, EBV, CMB, Influenza, Hepatitis A, B, or C; fungal infections such as those caused by the yeast genus *Candida*; parasitic infections such as those caused by schistosomes, filaria, nematodes, trichinosis or protozoa such as trypanosomes causing sleeping sickness, plasmodium causing malaria or leishmania causing leishmaniasis; and bacterial infections such as those caused by mycobacterium, corynebacterium, or staphylococcus. Hypersensitivity diseases include but are not limited to Type I hypersensitivities such as contact with allergens that lead to allergies, Type II hypersensitivities such as those present in Goodpasture's syndrome, and myasthenia gravis.

Therapeutic use of the T cell V region proteins of the invention is premised upon the correlation between a specific immune related disease and the preferential expression of a particular T cell antigen receptor V region gene product or the expanded usage of a particular T cell antigen receptor V gene. Though the present inventors do not wish to be bound by scientific theory, the T cell antigen receptor V regions are useful in part because it is possible to regulate the immune response in an individual by specific therapeutic intervention utilizing the T cell antigen receptor. Specifically, the presence or expression of a particular variable region locus has been shown to correlate with particular immune-related disorders. By determining the particular V region loci associated with a particular immune disorder one can treat the individual by inhibiting the attack by the T cells carrying the particular V region. Further, the T cell antigen receptor V region may affect immunosuppressive functions by stimulating regulatory T cells which will specifically interact with T cells bearing a targeted V region. It is also likely that the receptor subunit may elicit an antibody response that will specifically interact with the targeted V region and therefore be useful in modulating the immune response.

The T cell antigen receptor V region protein of the instant invention provide distinct advantages in the treatment of an immune related disease. Prior to the instant invention, therapeutic options for treatment of immune related disease with specific T cell involvement included: (a) no treatment with possible spontaneous resolution; (b) treatment with peptides corresponding to distinct segments of the T cell antigen receptor V region; c) nonspecific treatments such as steroids or non steroidal anti-inflammatory agents. However, none of these affords the particular advantage of the present invention. The therapeutic methods of the instant invention have the distinct advantage over the prior art methods of treating an immune related disease in that the methods of the present invention target only the particular T cell subset expressing a particular TCR V region and can be used across a diverse range of affected individuals since the invention provides for the elimination of the need to select a particular peptide based on the MHC haplotype of a particular individual. The method of the present invention more closely approaches the goal of modulating only disease related T cells while sparing or not affecting other T cells in the subject across a broad range of individuals. The invention therefore achieves a greater specificity of therapy across a wider population.

In a preferred embodiment the T cell antigen receptor V region protein may be used to down regulate or eliminate a subset of T cells that bear the T cell antigen receptor V region as produced by the present invention. The T cell antigen receptor V region protein can be used in a therapeutic situation to modulate the activity of those T cells bearing the targeted V region or to induce unresponsiveness in the actively responding population of T cells bearing the targeted V region. In this situation the T cell antigen receptor is used as a therapeutic composition in a subject.

As mentioned above, the therapeutic utility is premised on the preferential utilization of a particular T cell antigen receptor V region in a particular immune related situation. T cell antigen receptor V region proteins associated with a given disease are identified using any of a variety of techniques well known in the art. A genetic approach using patients known to have Myasthenia gravis or multiple sclerosis was described by Oksenberg, J. R., et al., 1989, Proc. Natl. Acad. Sci. USA 86:988–992.

The term treatment in the instant invention is meant to include the situations of "prevention," "suppression" or "treatment" of the disease. "Prevention" involves administration of the protective composition prior to the induction of the disease. Thus, for example, in the animal model, EAE, successful administration of a protective composition prior to injection of the encephalitogen that induces the disease results in "prevention" of the disease.

"Suppression" involves administration of the composition after the inductive event but prior to the clinical appearance of the disease. Again, using the EAE example, successful administration of a protective composition after injection of the encephalitogen, but prior to the appearance of neurological symptoms comprises "suppression" of the disease.

"Treatment" involves administration of the protective composition after the appearance of the disease. In the EAE example successful administration of a protective composition after injection of encephalitogen and after clinical signs have developed comprises "treatment" of the disease.

For measuring preventative, suppressive or therapeutic benefit of the TCR V region protein of the present invention certain clinical outcomes are measured. In particular alteration of proliferative response of lymphocytes in vitro can be measured. Assays for measuring the therapeutic benefit of the particular V region protein are known in the art.

Animal model systems which can be used to screen the effectiveness of the proteins in protecting against or treating the disease are available. Systemic lupus erythematosus (SLE) is tested in susceptible mice as disclosed by Knight et al., 1978, J.Exp. Med., 147:1653 and Reinersten et al., (1978) 299:515. Myasthenia Gravis (MG) is tested in SJL/J female mice by inducing the disease with soluble AChR protein from another species as described in Lindstrom et al., (1988) Adv. Immunol. 42:233–284. Arthritis is induced in a susceptible strain of mice by injection of Type II collagen as described by Stuart et al., (1984) Ann. Rev. Immunol., 42:233–284. Adjuvant arthritis is induced in susceptible rats by injection of Mycobacterial heat shock protein as described by Van Eden et al., (1988) Nature 331:171–173. Thyroiditis is induced in mice by administration of thyroglobulin as described by Maron et al., (1980) 152:1115–1120. Insulin dependant diabetes mellitus (IDDM) occurs naturally or can be induced in certain strains of mice such as those described by Kanasawa, et al., (1984). EAE in mouse and rat serves as a model for MS in human. In this model, the demyelinating disease is induced by administration of myelin basic protein as described by Paterson, P. Y. Textbook of Immunopathology (Mischer et al., eds.); Grune and Stratton, New York, pp 179–213 (1986); McFarlin, D. E. et al., (1973) Science 179:478–480: and Satoh, J., et al., J.Immunol., 138:179–184 (1987).

Of course, the identical proteins may not be effective in humans since they may not correspond to an appropriate site of the disease-associated human TCR. It is to be understood that modifications of the protein sequence delineated in a particular animal model may be required in order to treat subjects belonging to other species, including humans.

4. PHARMACEUTICAL COMPOSITIONS CONTAINING THE T CELL ANTIGEN RECEPTOR V REGION

The proteins and compositions of the present invention, or their functional derivatives, are well suited for the preparation of pharmaceutical compositions. The pharmaceutical compositions of the invention may be administered to any animal which may experience the beneficial effects of the compositions of the invention. Foremost among such animals are humans, although the invention is not intended to be so limited.

The pharmaceutical compositions of the present invention may be administered by any means that achieve their intended purpose. For example, administration may be by parenteral, subcutaneous, intravenous, intradermal, intramuscular, intraperitoneal, transdermal, or buccal routes. Alternatively, or concurrently, administration may be by the oral route. The proteins and pharmaceutical compositions can be administered parenterally by bolus injection or by gradual perfusion over time.

The dosage administered will be dependent upon the age, sex, health, and weight of the recipient, kind of concurrent treatment, if any, frequency of treatment, and the nature of the effect desired. The dose ranges for the administration of the compositions of the present invention are those large enough to produce the desired effect, whereby, for example, an immune response to the proteins as measured by delayed-type hypersensitivity (DTH) or antibody production, is achieved, and the immune-related disease is significantly prevented, suppressed, or treated. The doses should not be so large as to cause adverse side effects, such as unwanted cross reactions, generalized immunosuppression, anaphylactic reactions and the like.

Preferred doses for humans range between about 0.001–1 mg/kg body weight.

In addition to proteins of the invention which themselves are pharmacologically active, pharmaceutical compositions may contain suitable pharmaceutically acceptable carriers comprising excipients and auxiliaries which facilitate processing of the active compounds into preparations which can be used pharmaceutically. Preferred compositions include the inclusion of an adjuvant, such as alum, or other adjuvants known in the art. (See, for example, Warren et al., 1986, Ann. Rev. Immunol. 4:369–388; Chedid, L., 1986, Feder. Proc. 45:2531–2560.)

To enhance delivery or bioactivity, the proteins can be incorporated into liposomes using methods and compounds known in the art.

Preparations which can be administered orally in the form of tablets and capsules, preparations which can be administered rectally, such as suppositories, and preparations in the form of solutions for injection or oral introduction, contain about a 0.001 to about 99 percent, preferably from about 0.01 to about 95 percent of active compound(s), together with the excipient.

Suitable excipients are, in particular, fillers such as saccharides, for example lactose or sucrose, mannitol or sorbitol cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the proteins in water-soluble form, for example, water-soluble salts. In addition, suspensions of the proteins as appropriate oil injection suspensions may be administered. Suitable lipophilic solvents or vehicles include fatty oils, for example, sesame oil, or synthetic fatty acid esters, for example, ethyl oleate or triglycerides. Aqueous injection suspensions containing substances which increase the viscosity of the suspension include, for example, sodium carboxymethyl cellulose, sorbitol, and/or dextran. Optionally, the suspension may also contain stabilizers.

The proteins are formulated using conventional pharmaceutically acceptable parenteral vehicles for administration by injection. These vehicles are nontoxic and therapeutic, and a number of formulations are set forth in *Remington's Pharmaceutical Sciences*, (supra). Nonlimiting examples of excipients are water, saline, Ringer's solution, dextrose solution and Hank's balanced salt solution. Formulations according to the invention may also contain minor amounts of additives such as substances that maintain isotonicity, physiological pH, and stability.

The proteins of the invention are preferably formulated in purified form substantially free of aggregates and other protein materials, preferably at concentrations of about 1.0 ng/ml to 100 mg/ml.

Effective doses of the proteins of this invention for use in preventing, suppressing, or treating an immune-related disease are in the range of about 1 ng to 100 mg/kg body weight. A preferred dose range is between about 10 ng and 10 mg/kg. A more preferred dose range between about 100 ng and 1 mg/kg.

Methods to increase the effectiveness of proteins are known in the art. These techniques may be used in conjunction with the proteins of the instant invention.

The following examples are offered by way of illustration not limitation.

EXAMPLES

The following general techniques are used throughout the following Examples.

1. GENERAL MATERIALS AND METHODS

A. Bacteria, plasmids, and general methods

*Escherichia coli* GM2929, methylase-negative, and *E. coli* LJ24 (lac deletion) (Rasmussen et al. (1991) J. Bacteriology 173:6390–6397) were gifts from Dr. Martin Marinus, University of Massachusetts Medical School, Worcester, Mass. *E. coli* JM109 (Yanisch-Perron et al., (1985) Gene 33:103–119) were purchased from Promega Corporation, Madison, Wis. BL21 (lon$^-$, ompT$^-$) (Wood, W. B., (1966) J. Mol. Biol. 16:118–133; Studier and Moffatt, (1986) J. Mol. Biol. 189:113–130) were purchased from Novagen, Madison, Wis. SG22094 (lon$^-$, clp$^-$), SG21163 (lon$^-$, htpr$^-$) and SG21173 (lon$^-$, htpr$^-$, clp$^-$) were gifts from Dr. Susan Gottesman, National Institutes of Health, Bethesda, Md. Bacteria were made competent by the method of Morrison (1979, Meth. Enzymology 68:326–331) or were purchased (DH5α) from GibcoBRL, Gaithersburg, Md. pKK233-2 (Amann and Brosius, (1985) Gene 40:183–190) was purchased from Pharmacia, Piscataway, N.J. pBR322 (Bolivar et al., (1977) Gene 2:95–113) was from New England Biolabs, Beverly, Mass. pBluescript II KS+ (Alting-Mees et al., (1992) Meth. Enzymology 216:483–495) was from Stratagene, La Jolla, Calif. pDC952 containing the argU (dnaY) gene (Lindsey et al., (1989) J. Bacteriology 171:6197–6205) was a gift from Dr. James R. Walker, University of Texas, Austin, Tex. pSE420 (Brosius, (1992) Meth. Enzymology 216:469–483) and pKK480-3 (Brosius, (1992) supra) were gifts from Dr. Jürgen Brosius, Mount Sinai School of Medicine, New York, N.Y. pUCtS (Bukrinsky et al. (1988) Gene 70:415–417) was obtained from Michail I. Bukrinsky via Jürgen Brosius.

Plasmid constructions were performed by standard procedures (Sambrook et al., (1989) Molecular Cloning. A Laboratory Manual. Second Edition. Cold Spring Harbor Laboratory Press, Cold Spring Harbor, N.Y.) DNA restriction and modification enzymes were purchased from New England Biolabs, unless otherwise stated, and used according to the manufacturer's specifications. Synthetic oligonucleotides were purchased from Operon Technologies, Inc., Alameda, Calif., unless otherwise indicated. Oligonucleotides were annealed together by mixing equimolar concentrations of the complementary oligonucleotides in 10 mM Tris pH8.0, 5 mM MgCl$_2$ and placing in 100° C. for 5 min and then cooling slowly to 25° C. Polymerase chain reaction (PCR) was performed (Saiki et al., (1988) Science 239:487–491) in a Perkin Elmer Cetus DNA Thermal Cycler, using the GeneAmp reagent kit (The Perkin-Elmer Corporation, Norwalk, Conn.). DNA sequencing employed the dideoxynucleotide chain termination method (Sanger et al., (1977) Proc. Natl. Acad. Sci. USA 74:5463–5467) using the Sequenase kit (U.S. Biochemical, Cleveland, Ohio). All chemical reagents were of the highest purity available.

B. Growth and induction of cell cultures

For chemically induced cultures, frozen glycerol stocks were used to inoculate 5–25 ml 2XYT medium [16 g Bacto-Tryptone (Difco 0123), 10 g Bacto-Yeast Extract (Difco 0127), 10 g NaCl, pH 7.2–7.4, per liter water] containing 6 μg/ml tetracycline, and allowed to grow overnight at 37° C., 280 rpm. Typically, 1/100 volumes of the overnight culture were used to inoculate each of two 125-ml flasks containing 25 ml 2XYT medium plus 6 µg/ml tetracycline. Cultures were grown at 37° C., 280 rpm until $A_{580}$ was 0.5–1.0 absorbance units, and then induced with 1 mM isopropyl β-D-thiogalactopyranoside (IPTG), and allowed to grow for a further 2 hr.

For thermal induction, cultures were grown at 30° C., 280 rpm until $A_{580}$ was 0.5–1.0 absorbance units. Thereafter, one culture was maintained at 30° C., and the other was induced by transferring to a water bath at 42° C., and allowed to grow for a further 2 hr. Alternatively, a culture was induced by growing at 30° C. until $A_{580}$ was 0.3–0.6 absorbance units, and thereafter was divided into two aliquots; one was maintained at 30° C., and the other was allowed to grow at 42° C.

To assay for results of induction, duplicate samples equivalent to 1 ml of cells at $A_{580}=1.0$ were removed (e.g., assuming $A_{580}=3.0$, then 333 µl culture was removed). The samples were centrifuged in an Eppendorf microcentrifuge at 14,000 g, 1 min., the supernatants discarded, and the cell pellets were stored at −20° C.

C. Stability study

Bacteria were streaked to single colonies three successive times and a single colony from the third plate was inoculated into 200 ml 2XYT medium containing 6 µg/ml tetracycline. The culture was grown to $A_{580}=0.5–1.0$ absorbance units, and 60 ml were removed, mixed with 40 ml glycerol and 1 ml aliquots were distributed into 100 vials to be stored at −80° C. The remainder of the culture was divided into two aliquots; one was incubated uninduced, and the other was induced by IPTG addition or temperature shift. Both cultures were allowed to grow for a further 2 hr. Samples equivalent to 1 ml culture at $A_{580}=1.0$ were removed prior to and at 2 hr after induction, and assayed for $A_{580}$ absorbance, pH, and protein production by EIA, acrylamide gel electrophoresis, and Western blotting.

Three vials from the frozen bank were tested in parallel for bacterial growth and protein production: Each vial (1 ml) was inoculated into 200 ml 2XYT medium plus 6 µg/ml tetracycline, and incubated to $A_{580}=0.5–1.0$ absorbance units. Thereafter each culture was divided into two aliquots, one to be incubated uninduced, the other to be induced chemically or thermally. Samples equivalent to 1 ml culture at $A_{580}=1.0$ were removed from both cultures prior to and at 2 hr after induction and assayed as described above.

For the stability study, a 1-ml aliquot was removed from one of the three parallel cultures prior to induction, diluted 1/1000 in 2XYT medium, and 20 µl or 200 µl was inoculated into 200 ml 2XYT medium plus tetracycline, and allowed to grow to $A_{580}=0.5–1.0$ absorbance units. Thereafter the culture was divided into two aliquots; one was induced, and both were allowed to grow for a further 2 hr. Samples equivalent to 1 ml culture at $A_{580}=1.0$ were removed prior to and at 2 hr after induction and assayed as above.

D. Cell fractionation

The cells were pelleted by centrifugation at 7000 g, 7 min, and the supernatant (culture medium) was recentrifuged at 14,000 g, 5 min prior to electrophoresis. The cell pellet was resuspended in 20% (w/v) sucrose, 0.3M Tris-HCl pH 8.0, 1 mM EDTA using ⅓ of initial culture volume, incubated at 25° C. for 15 min, and centrifuged at 6000 g, 7 min. The supernatant was discarded, and protein located in the periplasm was released by osmotic shock (Nossal and Heppel, (1966) J. Biol. Chem. 241:3055–3062) by resuspending in ⅓ original volume cold water, and incubating at 0° C., 10 min. Following centrifugation at 9000 g, 10 min the supernatant was saved (periplasmic fraction); the cell pellet was resuspended in 1× TST (25 mM Tris-HCl pH 8.0, 200 mM NaCl, 1 mM EDTA, 10 ml/liter Tween 20), sonicated, centrifuged at 12000 g, 15 min, and the supernatant was saved (soluble cytosolic fraction).

E. Polyacrylamide gel electrophoresis

The frozen E. coli cell pellet was resuspended in 70 µl water by vigorous vortexing or by sonication at 0° C. (Sonic Dismembrator, Model 301, ARTEK Systems Corporation) three times each for 5 seconds, at power output 0.4. The disrupted cells were mixed with 70 µl 2× loading buffer (125 mM Tris-HCl, pH 6.8, 4% SDS, 20% glycerol, 10% β-mercaptoethanol, 0.002% Bromophenol Blue) (Laemmli, (1970) Nature 227:680–685.) Samples were incubated at 100° C., 5 min., centrifuged at 14,000 g, 30 seconds, and 10–15 µl aliquots were loaded onto pre-cast 16% or 10–20% acrylamide Tricine gels (Novex, San Diego, Calif.) and run in reservoir buffer obtained from the same manufacturer. Electrophoresis was at 125 V constant voltage, or 45 mA constant current, per two gels, for about 2 hr, until the bromophenol blue tracking dye was off the gels. Markers were prestained low molecular weight protein standards (#SE130024, Integrated Separation Systems, Natick, Mass.) used at 1 µl per lane. Gels were stained overnight in 10% acetic acid, 25% methanol, 0.025% Coomassie Brilliant Blue R.

F. Western blot analysis

Following separation by SDS-PAGE, proteins were immunodetected (Towbin et al., (1979) Proc. Natl. Acad. Sci. USA 76:4350–4354) by electrotransfer to polyvinylidene difluoride (PVDF) membranes (Immobilon-P, Millipore, Bedford, Mass.) using a Semi-Dry electroblotter (Integrated Separation Systems). Proteins were transferred at 10 mA per $cm^2$ membrane for 1–3 hr, and the membranes were blocked overnight in blocking buffer (1× PBS, 2% dried milk, 0.1% Tween-20).

The membranes were washed three times, 5 min each in 1× PBS, 0.1% Tween-20, followed by washing three times, 5 min each in 1× PBS, and then they were submerged in an HRP-conjugated monoclonal anti-Vβ5.3 antibody (13A2-HRP, 0.25 mg/ml) diluted 1:3000 in 1× PBS, 0.1% Tween-20. Following gentle agitation for 2 hr, the membranes were washed as described above, and the proteins were visualized with the Enhanced Chemiluminescence assay (Amersham, Arlington Heights, Ill.) used according to the manufacturer's instructions. Film exposure was between 5 seconds and 1 minute.

G. Enzyme immunoassay

The frozen cell pellets were resuspended by vigorous vortexing in 20 µl 8M urea, 50 mM Tris-HCl, pH 8.5, (Marston and Hartley, (1990) Meth. Enzymology 182:264–276) and Vβ5.3 was quantified by enzyme immunoassay as follows:

Nunc-Immuno Maxisorp plates (VWR #62409-002) were coated with 100 µl/well 4C2 IgG at 4 µg/ml in PBS, and stored at 4° C. overnight. The coating solution was discarded, and blocking buffer (1% casein hydrolysate in PBS, 0.05% Tween-20) was added at 200 µl/well. The plates were incubated at room temperature for 2 hr, 150 rpm, and then washed three times with wash buffer (PBS, 0.05% Tween-20). Samples (diluted 1/2,000 to 1/32,000) and Vβ5.3 standards in blocking buffer were added at 100 μl/well, and incubated at room temperature for 90 min, 150 rpm. The plates were washed three times with wash buffer, and an HRP-conjugated anti-Vβ5.3 monoclonal antibody (13A2-HRP) diluted 1/500 in blocking buffer plus 5% fetal bovine serum was added at 100 μl/well (0.5 μg/ml). The plates were incubated at room temperature for 90 min, 150 rpm, washed four times, and 100 μl/well O-Phenylenediamine (OPD) substrate was added. After 30 min, the reaction was terminated by adding 50 μl 2N $H_2SO_4$ per well. The absorbance was measured at 490 nm minus the background absorbance at 650 nm. Blank wells did not contain sample.

2. CONSTRUCTION OF PLASMIDS

EXAMPLE 1

Construction of pK2D

The starting point for the expression of the T cell antigen receptor V region proteins of the invention was the construction of a plasmid that contained the proper regulatory elements for expression of the T cell antigen receptor V region protein. These elements include the promoter, a transcription terminator, an origin of replication for stable replication in bacteria. Additionally because of regulatory concerns associated with the manufacture of a protein for which one possible indication is the in vivo use in a therapeutic setting, a gene coding for resistance to tetracycline was chosen to facilitate selection of plasmid bearing cells. Finally, the starting expression vector required a multiple cloning site, strategically engineered to facilitate the cloning of the preferred gene sequences of the invention into the expression vector. The following example describes the unique starting plasmid of the invention.

The starting point for the construction of preferred expression vector was pKK233-2 (4.6 kb), described supra. The NcoI restriction site was converted to a SpeI site as follows: pKK233-2 was digested with NcoI, and the resulting 5' protruding ends were removed by incubation with mung bean nuclease at 25° C. for 30 min. The plasmid was extracted twice with phenol-chloroform, precipitated with ethanol in the presence of 2M ammonium acetate, and resuspended in water. Following dephosphorylation with bacterial alkaline phosphatase (GibcoBRL) the vector was ligated to a synthetic SpeI linker (#1085, New England Biolabs), and the ligation mix was transformed into DH5α competent cells to yield vector pKK233-2A.

Next, the tetracycline gene was restored as follows: pKK233-2A (4.6 kb) was digested with EcoRI and SalI yielding two fragments, 279 bp and 4321 bp each. The two fragments were separated by agarose gel electrophoresis, and the large fragment was purified from agarose using the Geneclean Kit (BIO 101, La Jolla, Calif.). A 651-bp fragment containing the amino-terminal coding region of the tetracycline gene was excised with EcoRI and SalI from pBR322, and ligated to the 4321-bp fragment from pKK233-2A. The resulting plasmid pK2B (4.97 kb) conferred tetracycline resistance on E. coli DH5α cells, and was further modified to delete a portion of the β-lactamase gene and convert the HindIII site into a SacII site, as follows:

A DNA segment spanning the unique SpeI site to the 3' terminus of the transcription terminators was PCR-synthesized using pK2B as template. The 5' "sense" primer contained restriction enzyme recognition sequences for SpeI, PstI and SacII in the 5' to 3' direction, underlined:

5'-TATAATGACTAGTCGCTGCAGCCAACCGCGGC TG-3' [SEQ ID NO 1]The 3' "antisense" primer contained a ScaI site, underlined:

5'-GTCCTAGAGTACTGAGCGGATAC-3' [SEQ ID NO 2]1 ng of pK2B DNA template was mixed in a reaction volume containing 10 mM Tris-HCl pH 8.3, 50 mM KCl, 1.5 mM $MgCl_2$, 100 μg/ml gelatin, 200 μM each of the deoxynucleotides (dATP, dCTP, dGTP, dTTP), 1 μM each of the two primers, and 2.5 units AmpliTaq DNA polymerase. The final reaction volume was 100 μl, overlaid with 100 μl mineral oil. The DNA was denatured at 95° C. for 2 min, and amplification was achieved with 30 cycles of 1 min at 95° C. for denaturation, 1 min at 60° C. for annealing, and 1 min at 72° C. for primer extension. The amplified DNA was analyzed on 1% agarose gel run in 40 mM Tris-HCl pH 7.8, 5 mM NaAcetate, 1 mM EDTA.

The resulting 485-bp PCR-synthesized fragment was digested with SpeI and ScaI, and ligated to a 4129-bp fragment that was obtained by digestion of pK2B with SpeI and ScaI resulting in a plasmid called pK2C.

Plasmid pK2C (4.6 kb) was further modified to contain a multiple cloning site. First, pK2C was digested with SpeI and SacII, and ligated to a double-stranded synthetic oligonucleotide containing 15 restriction sites. This multiple cloning site (MCS) was formed by annealing equimolar concentrations of two complementary synthetic oligonucleotides, 91 and 97 bp long, respectively, having the following sequence:

5'-GGCTCGAGCCTAGGCTGCAGCCCGGGGCGCG CGCGGCCGCAGGCC TTTAATTAAGAGCTCCG-GACCGCACAATGTGGGCGCGCCCTTAAGA-3' [SEQ ID NO 3]

5'-CTAGTCTTAAGGGCGCGCCCACATTGTGCGGT CCGGAGCTCTTAA TTAAAGGCCTGCGGC-CGCGCGCGCCCCGGGCTGCAGCCTAGGCTCG AG CCGC-3' [SEQ ID NO 4]The MCS codes for the following restriction enzymes sites: SpeI, AflIII, AscI, DraIII, RsrII, SacI, PacI, StuI, NotI, BssHII, XmaI, PstI, AvrII, XhoI, and SacII. The ligation mix was transformed into methylase-negative E. coli GM2929. The resulting plasmid pK2D (4.67 kb) was partially sequenced to ensure the integrity of the in vitro synthesized regions.

Results

The starting plasmid was pKK233-2 which contains the following elements: The trc promoter (Brosius et al., (1985) J. Biol. Chem. 260:3539–3541) which is similar to the tac promoter derived by fusing the −10 region of the lacUV5 promoter with the −35 region of the tryptophan promoter (de Boer et al., (1983) Proc. Natl. Acad. Sci. USA 80:21–25; Amann et al., (1983) Gene 25:167–178); the trc promoter is identical to the tac promoter with the exception of a 1 base pair change in the promoter (Brosius et al., (1985) supra). The plasmid also contains a ribosome binding site followed by a cloning site of three unique restriction enzymes (NcoI, PstI and HindIII). followed by the transcription terminators of the rrnB ribosomal RNA operon of E. coli (Brosius et al., (1981) Plasmid 6:112-118). In addition, pKK233-2 contains the β-lactamase gene for ampicillin resistance, the pBR322 origin of replication, and a small non-functional carboxyl terminal fragment from the tetracycline resistance gene.

pKK233-2 was modified in order to destroy the NcoI site; restore the tetracycline resistance gene; delete a segment of the β-lactamase coding region, thus inactivating the gene;

and insert a multiple cloning site consisting of 15 restriction sites to produce pK2D.

EXAMPLE 2

Plasmid pK2D was further modified to incorporate either the pelB signal sequence from *Erwinia carotovora* (Lei et al., (1987) J. Bacteriology 169:4379–4383) or the heat stable enterotoxin II (STII) signal sequence of *Escherichia coli* (Morioka-Fujimoto et al., (1991) J. Biol. Chem. 266:1728–1732.)

Construction of pK-pelB

Plasmid pK2D (4.67 kb) was engineered to include a ribosome binding site (Shine and Dalgarno, (1974) Proc. Natl. Acad. Sci. USA 71:1342–1346; Shine and Dalgarno, (1975) Nature 254:34–38; Steitz and Jakes, (1975) Proc. Natl. Acad. Sci. USA 72:4734–4738) and the pelB signal sequence from *E. carotovora* (Lei et al., (1987) supra) to create plasmid pK-pelB (4.74 kb), as follows:

pK2D was digested with SpeI and SacI located in the MCS, and the vector was ligated to two complementary synthetic oligonucleotides, 103 bp and 95 bp long, respectively, having the sequence shown below. A silent mutation (lower case letters) was introduced into the pelB sequence, in order to create an NcoI restriction site, underlined, facilitating the subsequent subcloning of the Vβ5.3 gene sequence. 5'-CTAGTAAATTCTATTTCAAGGAGACAGT-CATAATGAAATACC TATTGCCTACGGCAGCCGCTG-GATTGTTATTACTCGCTGCCCAACCA GCcATGGC-CGAGCT-3' [SEQ ID NO 5]

5'-CGGCCATgGCTGGTTGGGCAGCGAG-
TAATAACAATCCAGCGGCT GCCGTAGGCAAT-
AGGTATTTCATTATGACTGTCTCCT-
TGAAATAGA ATTTA-3' [SEQ ID NO 6]

Construction of pK-STII

Plasmid pK2D was engineered to include a ribosome binding site and the heat-stable enterotoxin (STII) signal sequence of *E. coli* (Morioka-Fujimoto et al., (1991) supra), as follows:

pK2D was digested with SpeI and DraIII located in the MCS, and the vector was ligated to two complementary synthetic oligonucleotides, 105 bp and 98 bp long, respectively, having the sequence shown below. Two silent mutations (lower case letters) were introduced into the STII sequence, in order to create MluI and DraIII restriction sites, underlined, facilitating the subsequent subcloning of Vβ5.3.

5'-CTAGTAAATTCTATTTCAAGGAGACAGT-
CATAATGAAAAAGAA TATAGCATTCCTAC-
TAGCTTCAATGTTCGTCTTCTCTATTGCAACTA
ACGCgTACGCaCATT-3' [SEQ ID NO 7]

5'-GtGCGTAcGCGTTAGTTGCAATAGAGAA-
GACGAACATTGAAGCT AGTAGGAATGCTATAT-
TCTTTTTCATTATGACTGTCTCCTTGAAATA
GAATTTA-3' [SEQ ID NO 8]

EXAMPLE 3

The plasmids containing the signal sequences from Example 2 supra were further modified to include two regulatory elements.

Construction of pKT-pelB

Plasmid pK-pelB was further modified to include two regulatory elements upstream of the pelB leader, to create pKT-pelB (4.8 kb). These elements are the translational enhancer from the bacteriophage T7 gene 10 (g10), and a mini-cistron coding for 8 amino acid residues. Insertion of the two regulatory elements was achieved by digestion of pK2D with SpeI and SacI, followed by ligation of the vector to synthetic oligonucleotides coding for the g10 sequence, the ribosome binding site, a mini-cistron and the pelB leader, in the 5' to 3' direction. The oligonucleotides were synthesized as two complementary sets of 71–89 mers that could be ligated via complementary 9 bp overhangs between the pairs of oligonucleotides. The two complementary pairs of oligonucleotides were designated Pair A (oligos J5A+J6A, 89 bp and 76 bp, respectively) and Pair B (oligos J5B+J6B, 71 bp and 76 bp, respectively) having the following sequence:

J5A

5'-CTAGTCCGGAATTGGGCATCGAT-
TAACTTTATTATTAAAAATTAA AGAGGTATATAT-
TAATGTATCGATTAAATAAGGAGGAATAAATA-3'
[SEQ ID NO 9]

J6A

5'-CTCCTTATTTAATCGATACAT-
TAATATATACCTCTTTAATTTTTA ATAATAAAGT-
TAATCGATGCCCAATTCCGGA-3' [SEQ ID NO 10]

J5B

5'-ATGAAATACCTATTGCCTACGGCAGC-
CGCTGGATTGTTATTACTC GCTGCCCAAC-
CAGCCATGGCCGAGCT-3' [SEQ ID NO 11]

J6B

5'-CGGCCATGGCTGGTTGGGCAGCGAG-
TAATAACAATCCAGCGGCTG CCGTAGGCAAT-
AGGTATTTCATTATTTATTC-3' [SEQ ID NO 12]

Construction of pKT-STII

Plasmid pK-STII was further modified to include the same two regulatory elements as in pKT-pelB, thus creating pKT-STII (4.8 kb). pK2D was digested with SpeI and DraIII, and the vector was ligated to synthetic oligonucleotides coding for the g10 sequence, the ribosome binding site, a mini-cistron and the STII leader, in the 5' to 3' direction. The oligonucleotides were synthesized as two complementary sets of 73–89 mers that could be ligated via complementary 9 bp overhangs between the pairs of oligonucleotides. The two complementary pairs of oligonucleotides were designated Pair A (oligos J5A+J6A, 89 bp and 76 bp, respectively) and Pair B (oligos J5C+J6C, 73 bp and 79 bp, respectively) having the following sequence:

J5A

5'-CTAGTCCGGAATTGGGCATCGAT-
TAACTTTATTATTAAAAATTAA AGAGGTATATAT-
TAATGTATCGATTAAATAAGGAGGAATAAATA-3'
[SEQ ID NO 9]

J6A

5'-CTCCTTATTTAATCGATACAT-
TAATATATACCTCTTTAATTTTTA ATAATAAAGT-
TAATCGATGCCCAATTCCGGA-3' [SEQ ID NO 10]

J5C

5'-ATGAAAAAGAATATAGCATTCCTAC-
TAGCTTCAATGTTCGTCTT CTCTATTGCAAC-
TAACGCGTACGCACATT-3' [SEQ ID NO 13]

J6C

5'-GTGCGTACGCGTTAGTTGCAATAGAGAA-
GACGAACATTGAAGC TAGTAGGAATGCTATAT-
TCTTTTTCATTATTTATTC-3' [SEQ ID NO 14]

EXAMPLE 4

Construction of pK-pelB-Vβ5.3

The next step in the expression of the T cell antigen receptor Vβ5.3 protein was the incorporation of the Vβ5.3 sequence into the plasmids containing the signal sequences described in Example 2 supra.

The complete nucleotide sequence of Vβ5.3 was generated as follows: the DNA sequence of Vβ5.3 clone 12A1 was originally published by Leiden et al. and later in corrected form (Leiden et al. (1986) Proc. Natl. Acad. Sci. USA 83:4456–4460.) This clone 12A1 was missing nucleotide coding for the N-terminal four amino acid residue; in addition, the deduced N-terminal 3 amino acid residues of clone 12A1 were incorrect. The N-terminal amino acid sequence of Vβ5.3 (HPB-ALL) was published by Jones et al. ((1984) Science 227:311–314) without specifying the N-terminal first amino acid residue, which was later determined to be Glycine (Jeff Leiden, unpublished). Using the above sequence information, the complete Vβ5.3 was reconstructed by recombinant DNA techniques. The resulting plasmid (pBB-Vβ5.3) was the source of the Vβ5.3 sequence for the following examples. The amino acid sequence of the Vβ5.3 is shown in FIG. 1 [SEQ ID NO. 27].

Vβ5.3 was PCR-synthesized using pBB-Vβ5.3 (6.2 kb) as template. The 5' "sense" primer contained an NcoI restriction enzyme site, underlined:

5'-TAATTAGCCATGGCCGGCGTAAC-CCAATCTCCG-3' [SEQ ID NO 15] The 3' "antisense" primer was complementary to a region downstream of a PstI site in the vector:

5'-CCAGTGCCAAGCTTGCATGCC-3' [SEQ ID NO 16] The resulting Vβ5.3 fragment was blunt-ended using the Klenow fragment of DNA polymerase I, and ligated into the dephosphorylated EcoRV site of pBluescript II KS+ to yield plasmid pBL-pelB-Vβ5.3. The Vβ5.3 insert was excised by digestion with NcoI and PstI, purified from agarose, and ligated into the NcoI and PstI sites of pK-pelB, yielding plasmid pK-pelB-Vβ5.3 (5 kb).

Construction of pK-STII-Vβ5.3

Vβ5.3 was PCR-synthesized using pBB-Vβ5.3 (6.2 kb) as template. The 5' "sense" primer contained an MluI restriction enzyme site, underlined:

5'-GAAATTAACGCGTACGCAGGCGTAAC-CCAATCTC-3' [SEQ ID NO 17] The 3' "antisense" primer was complementary to a region downstream of a PstI site in the vector:

5'-CCAGTGCCAAGCTTGCATGCC-3' [SEQ ID NO 18] The resulting Vβ5.3 fragment was blunt-ended using the Klenow fragment of DNA polymerase I, and ligated into the dephosphorylated EcoRV site of pBluescript II KS+ to yield plasmid pBL-STII-Vβ5.3. The Vβ5.3 insert was excised by digestion with MluI and PstI, purified from agarose, and ligated into the MluI and PstI sites of pK-STII, yielding plasmid pK-STII-Vβ5.3 (5 kb).

Results

Vβ5.3 fused to the pelB or the STII leaders was expressed in E. coli JM109 (TABLE I). Induction was for 2 hr. and Vβ5.3 yields were measured by EIA.

TABLE 1

| | EXPRESSION AND COMPARTMENTATION OF Vβ5.3 | | | |
|---|---|---|---|---|
| | pK-pelB-Vβ5.3 | | pK-STII-Vβ5.3 | |
| Compartment | 0 mM IPTG | 1 mM IPTG | 0 mM IPTG | 1 mM IPTG |
| Supernatant | 0 µg/ml | 1.3 µg/ml | 0.5 µg/ml | 2.2 µg/ml |
| Periplasm | 0.9 | 4.6 | N.D. | 5.5 |
| Cytosol | 9.9 | Off scale [1:40] | 2.0 | Off scale [1:40] |

Both leaders were functional, although most of the expressed protein was localized intracellularly. The STII leader appeared to be somewhat more efficient for secretion, and all subsequent Vβ5.3 constructs utilized the STII leader for secreted expression.

EXAMPLE 5

This Example details the plasmids containing the leader sequence and the two regulatory elements (g10 and minicistron) as well as the Vβ5.3 sequence.

Construction of pKT-pelB-Vβ5.3

Plasmid pKT-pelB-Vβ5.3 was constructed by excision of the Vβ5.3 insert from pK-pelB-Vβ5.3 using NcoI and PstI, and ligation into the NcoI and PstI sites of pKT-pelB.

Construction of pKT-STII-Vβ5.3

Plasmid pKT-STII-Vβ5.3 was similarly constructed by excision of the Vβ5.3 insert from pK-STII-Vβ5.3 using MluI and PstI, and ligation into the MluI and PstI sites of pKT-STII.

All subsequent plasmid constructs utilized the STII signal sequence. Therefore, where the signal sequence is not specified, it is understood that the STII sequence was utilized.

Results pKT-Vβ5.3

Plasmid pK-STII-Vβ5.3 (Example 4) was modified to include two regulatory elements upstream of the STII leader, to create pKT-Vβ5.3. These elements are the translational enhancer from the bacteriophage T7 gene 10 (g10), and a mini-cistron coding for 8 amino acid residues. Both elements have been demonstrated to enhance translational efficiency of several genes, presumably by attenuating secondary structures (Schoner et al., (1984) Proc. Natl. Acad. Sci. USA 81:5403–5407, Schoner et al. (1986) Proc. Natl. Acad. Sci. USA 83:8506–8510; Olins et al., (1988) Gene 73:227–235; Olins and Rangwala, (1989) J. Biol. Chem. 264:16973–16976).

pKT-Vβ5.3 provided up to 8-fold higher protein yields than pK-Vβ5.3 (Example 4) in *E. coli* JM109 under conditions of IPTG induction. The EIA values reported here are approximations, due to the lack of a pure Vβ5.3 standard at this time. pKT-Vβ5.3 was shown to be stable in *E. coli* JM109 for fermentation.

EXAMPLE 6

Construction of pKTB-Vβ5.3

A further modification to pKT-Vβ5.3 (Example 5) for secreted expression involved elimination of the IPTG requirement for induction. The existence of a lacIts gene coding for temperature-sensitive lac repressor (Bukrinsky et al., (1988) Gene 70:415–417) makes it possible to control gene expression from the trc promoter by elevating the temperature from 30° C. to 42° C. This would obviate the need to use IPTG or bacterial strains harboring the lacI or lacI$^q$ genes.

The lacIts gene was excised from pUCts by EcoRI digestion. The 1.7 kb fragment containing the entire lacIts-coding region and its associated regulatory elements, flanked by vector sequence, was blunt-ended with Klenow, and ligated into the dephosphorylated ScaI site, located downstream of the rrnB operon in pKT-Vβ5.3, yielding plasmid pKTB-Vβ5.3 (6.8 kb). The orientation of the lacIts gene was determined by restriction mapping.

Results

The lacIts gene was inserted in either orientation downstream of the rrnB transcription terminator in pKT-Vβ5.3 to create plasmid pKTB-Vβ5.3 (FIG. 2). This was expressed in *E. coli* LJ24 (lac deletion) and the protein was analyzed by Coomassie Blue staining on acrylamide gels (Laemmli, (1970, supra) and by Western blot (Towbin et al., (1979) supra). One orientation of the lacIts gene (transcription direction toward the Amp$^r$ region) clearly resulted in higher Vβ5.3 yield than the reverse orientation.

The putative Vβ5.3 band obtained from extracts of total cellular pellets was electrotransferred to Immobilon-P membranes, and visualized by Coomassie Blue staining. The band was excised and subjected to NH$_2$-terminal amino acid sequencing (Matsudaira, (1987) J. Biol. Chem. 262:10035–10038) to yield a total of 10 amino acid residues. These matched precisely the sequence of the N-terminal 10 amino acid residues of the processed Vβ5.3, i.e. no leader sequence was detected.

This plasmid was also expressed by thermal induction in three different bacterial strains, each of which contains increasing levels of endogenous lac repressor, i.e. LJ24<DH5α<JM109. Supernatants from induced cultures were assayed for Vβ5.3 expression by EIA (Table II)

The data agree with Western blot observations and predicted results, i.e. the highest expression level was achieved in LJ24 (ΔlacI) and the lowest in JM109 (lacI$^q$). In addition, Vβ5.3 yield by thermal induction was apparently higher than that observed by IPTG induction.

DNA sequencing of the lacIts gene

The entire coding sequence (1,083 base pairs) of the temperature-inducible lacIts gene plus the upstream 80 nucleotides including the promoter were sequenced and compared to the published sequence of the IPTG-inducible lacI gene (Farabaugh, (1978) Nature 274:765–769).

Nucleotide #559 (with reference to the start codon) changed from G to A, causing amino acid residue #187 to change from Glycine to Serine. In addition, nucleotide #857 changed from C to T, causing amino acid residue #286 to change from Serine to Leucine. However, on sequencing the same two regions in the lacI$^q$ gene in plasmid pSE420 (Brosius, (1992) supra) we confirmed only the former mutation (#559). Thus, the published sequence of the lacI gene (Farabaugh, (1978) supra) as well as that in Genebank (locus ECOLAC) is in error at position #857.

The promoter region of the lacIts gene was also sequenced, and found to be the same as that of the wild type lacI, and not lacI$^q$, gene (Calos, M. P. (1978) Nature 274:762–765).

We conclude that the lacIts gene differs from the wild type lacI gene by a single amino acid residue (#187), and this change imparts thermal sensitivity to the lacI repressor protein.

EXAMPLE 7

Construction of pKTB

Plasmid pKTB-Vβ5.3 (6.7 kb) was digested with SalI and PstI, and the 5.42 kb fragment was purified from agarose using the Geneclean Kit (BIO 101). Plasmid pKT-STII (4.8 kb) was digested with SalI and PstI, and the 1.15 kb fragment was similarly purified, and ligated to the 5.42 kb fragment, yielding plasmid pKTB (6.56 kb).

EXAMPLE 8

Construction of pKB-Vβ5.3

This plasmid is identical to pKTB-Vβ5.3 minus the two regulatory elements, i.e. the g10 translational enhancer and the mini-cistron. Plasmid pKTB (6.56 kb) was digested with SalI and PstI, and the large fragment (5.4 kb) was purified from agarose using the Geneclean Kit (BIO 101). Plasmid

TABLE 2 pKTB-Vβ5.3 EXPRESSION IN DIFFERENT BACTERIAL STRAINS

| Plasmid | Regulation | *E. coli* Host | Induction | Uninduced | Induced |
|---|---|---|---|---|---|
| pKTB-Vβ5.3 | lacIts | JM109 (lacI$^q$) | 42° C. | N.D. | 0.5 |
| pKTB-Vβ5.3 | lacIts | DH5α (lacI) | 42° C. | N.D. | 5.0 |
| pKTB-Vβ5.3 | lacIts | LJ24 (ΔlacI) | 42° C. | N.D. | 5.2 |
| pKT-Vβ5.3 | lacI$^q$ | JM109 | 2 mM IPTG | 0 | 0.9 |
| pKT | lacI$^q$ | JM109 | 42° C. | N.D. | 0 |

Cells were induced for 2 hr., and Vβ5.3 yields (μg/ml) were measured in culture supernatants.

pK-Vβ5.3 (4.9 kb) was digested with SalI and PstI, and the 1.3-kb fragment was similarly purified, and ligated to the 5.4-kb fragment, yielding plasmid pKB-Vβ5.3 (6.7 kb).
Results pKB-Vβ5.3

As discussed above, the addition of two regulatory elements, i.e. the g10 gene segment and the mini-cistron, appeared to enhance Vβ5.3 yield under conditions of IPTG induction. We wished to remove these two elements from the pKTB-Vβ5.3 vector, and reexamine Vβ5.3 yield under conditions of thermal induction. A comparison of pKTB-Vβ5.3 and pKB-Vβ5.3 by acrylamide electrophoresis and Western blotting showed that Vβ5.3 yield was unaffected by the removal of these two elements. EIA measurements of whole cell urea extracts showed that pKB-Vβ5.3 produced more protein than pKTB-Vβ5.3 when expressed in *E. coli* LJ24

TABLE 3

EXPRESSION OF Vβ5.3 IN DIFFERENT BACTERIAL STRAINS

| Plasmid | LJ24 | SG22094 | SG21163 | SG21173 |
|---|---|---|---|---|
| pKTB-Vβ5.3<br>+ leader<br>+ g10/MC | $9 \times 10^5$ | $8 \times 10^5$ | $2 \times 10^5$ | $3 \times 10^5$ |
| pKB-Vβ5.3<br>+ leader<br>− g10/MC | $11 \times 10^5$ | $5 \times 10^5$ | $4 \times 10^5$ | $2 \times 10^5$ |
| pKTBi-Vβ5.3<br>− leader<br>+ g10/MC | $0.6 \times 10^5$ | $10 \times 10^5$ | $10 \times 10^5$ | $10 \times 10^5$ |
| pKBi-Vβ5.3<br>− leader<br>− g10/MC | $1 \times 10^5$ | $17 \times 10^5$ | $13 \times 10^5$ | $39 \times 10^5$ |

Induction period: 2 hr at 42° C.
Culture volume: 25 ml
Leader: STII
g10: T7 gene 10
MC: Mini-cistron
Samples: Whole cell urea extracts
Vβ5.3 yields (units/ml) are approximations, as measured by EIA. 1 mg Vβ5.3 is approximately equivalent to $1 \times 10^6$ units.

Plasmid pKB-Vβ5.3 was demonstrated to be stable for fermentation.

EXAMPLE 9

Construction of pKB

Plasmid pKTB (6.56 kb) was digested with SalI and PstI, and the large fragment (5.4 kb) was purified from agarose using the Geneclean Kit (BIO 101). Plasmid pK-STII (4.75 kb) was digested with SalI and PstI, and the 1.1-kb fragment was similarly purified, and ligated to the 5.4-kb fragment, yielding plasmid pKB (6.5 kb).

EXAMPLE 10

Construction of pKTBi

This plasmid is identical to pKTB minus the STII signal sequence. pKTB (6.56 kb) was digested with SpeI and XmaI, and ligated to a double-stranded synthetic oligonucleotide coding for the g10 translational enhancer, a ribosome binding site, and a mini-cistron containing a second ribosome binding site. Restriction sites for NcoI, DraIII, RsrII and XmaI were designed in the 3' end. The two complementary oligonucleotides had the following sequence:

5'-CTAGTCCGGAATTGGGCATCGAT-
TAACTTTATTATTAAAAATTA AAGAGGTATATAT-
TAATGTATCGATTAAATAAGGAGGAATAAACC
ATGGCACATTGTGCGGTCCGC-3' [SEQ ID NO 19]

5'-CCGGGCGGACCGCACAATGTGCCATG-
GTTTATTCCTCCTTATTTA ATCGATACAT-
TAATATATACCTCTTTAATTTT-
TAATAATAAAGTTA
ATCGATGCCCAATTCCGGA-3' [SEQ ID NO 20]

EXAMPLE 11

Construction of pKBi

This plasmid is identical to pKB minus the STII signal sequence. pKTB (6.56 kb) was digested with SpeI and DraIII, and ligated to a double-stranded synthetic oligonucleotide containing a ribosome binding site, and NcoI and DraIII sites designed in the 3' end. The two complementary oligonucleotides had the following sequence:

5'-CTAGTAAATTATATTTAAAGGAG-
GAATAAACCATGGCACATT-3' [SEQ ID NO 21]
5'-GTGCCATGGTTTATTCCTCCTT-
TAAATATAATTTA-3' [SEQ ID NO 22]

EXAMPLE 12

Construction of pKTBi-Vβ5.3

This plasmid is identical to pKTB-Vβ5.3 minus the STII signal sequence. pKTBi (6.4 kb) was digested with XmaI and NcoI and ligated to PCR-synthesized Vβ5.3 using pKTB-Vβ5.3 as template. The 5' "sense" primer contained an NcoI restriction enzyme site, underlined:

5'-TATAGTCCATGGGCGTAACC-3' [SEQ ID NO 23]The 3' "antisense" primer contained an XmaI site, underlined:

5'-AACTTCCCGGGTTATCATTAGCTGC-3' [SEQ ID NO 24]

Results pKTBi-Vβ5.3

In parallel with the above work, we proceeded to remove the STII leader from the expression plasmid. Since most of the expressed Vβ5.3 is retained intracellularly (also see below) we thought that scale-up of this construct might yield a heterogeneous population of Vβ5.3 molecules, i.e. plus and minus leader, which would complicate subsequent purification of the processed Vβ5.3. Therefore, the STII leader was removed to create pKTBi-Vβ5.3 for intracellular expression. The expressed Vβ5.3 is expected to contain an N-terminal methionine, although this amino acid might be removed by endogenous methionine aminopeptidases (Ben-Bassat et al., (1987) J. Bacteriology 169:751–757; Baneyx and Georgiou, (1992), Expression of Proteolytically Sensitive Polypeptides in *Escherichia coli*. In Stability of Protein Pharmaceuticals, Part A: Chemical and Physical Pathways of Protein Degradation, Edited by Tim J. Ahern and Mark C. Manning. Plenum Press, New York, pp. 69–108) as observed for pKBi-Vβ5.3 (below).

pKTBi-Vβ5.3 was completed, but it failed to express protein in *E. coli* LJ24. The entire Vβ5.3 insert was sequenced and determined to be unambiguously correct. Plasmid DNA isolated post-induction and analyzed by restriction digestion appeared to be unaltered. We hypothesized that removal of the leader destabilizes Vβ5.3, and leads to its rapid proteolysis.

Therefore, we transformed pKTBi-Vβ5.3 into the protease-deficient strains SG22094 (lon⁻, clp⁻), and BL21 (lon⁻, ompT⁻) which gave decreasing yields in the order of SG22904>BL21. We also investigated the effect of different induction temperatures on yield: for both strains 42° C. was optimal. In addition, there was no significant increase in production between 2 and 5 hr.

pKTBi-Vβ5.3 was expressed in two additional protease-deficient strains: SG21163 (lon⁻, htpr⁻) and SG21173 (lon⁻, htpr⁻, clp⁻). The results are summarized in Table 3 (supra).

EXAMPLE 13

Construction of pKBi-Vβ5.3

This plasmid is identical to pKTBi-Vβ5.3 minus the g10 element and the mini-cistron. pKBi (6.43 kb) was digested with NcoI and SalI, and a 970 bp fragment was purified from agarose. pKTBi-Vβ5.3 (6.75 kb) was digested with NcoI and SalI and the 5.68 kb fragment was similarly purified, and ligated to the 970 bp fragment, yielding plasmid pKBi-Vβ5.3 (6.64 kb).

pKBi-Vβ5.3

This leaderless Vβ5.3 construct minus the two regulatory elements was successfully expressed in protease-deficient strains; our observations are similar to those for pKTBi-Vβ5.3. pKBi-Vβ5.3 was expressed in two additional protease-deficient strains: SG21163 (lon⁻, htpr⁻) and SG21173 (lon⁻, htpr⁻, clp⁻). The results are summarized in Table 3. pKBi-Vβ5.3 consistently produced more protein than pKTBi-Vβ5.3 in all strains tested (Table V). N-terminal sequencing of the expressed protein showed that the first 17 amino acid residues matched the expected Vβ5.3 sequence, and the terminal methionine residue was absent. The plasmid was also demonstrated to be stable.

A culture of *E. coli* transformed with plasmid pKBi-Vβ5.3 was deposited with the American Type Culture Collection (ATCC), 12301 Parklawn Drive, Rockville, Md. 20852 on Jan. 6, 1995 and assigned accession number 69739.

The present invention is not meant to be limited in scope by the specific embodiments described herein. Indeed, various modification of the invention in addition to those described herein will become apparent to those skilled in the art from the foregoing description and the accompanying figures. Such modification are intended to fall within the scope of the appended claims. Various publication are incorporated by reference in their entirety.

---

We claim:

1. A method for producing a recombinant T cell antigen receptor Vβ5.3 protein which comprises;
  a) transforming a competent bacterial host cell with a recombinant expression vector containing an inducible bacterial promoter and a coding region for a T cell antigen receptor Vβ5.3 protein free of extraneous Vβ protein sequences, operably linked in a 5' to 3' orientation;
  b) inducing the transformed bacterial host cell of step a, and;
  c) recovering the T cell antigen receptor Vβ5.3 protein.

2. The method of claim 1 wherein the inducible bacterial promoter is subject to chemical regulation.

3. The method of claim 2 wherein the expression vector further comprises a regulatory gene sequence which regulatory gene sequence is selected from the group consisting of the lacI gene or the lacIq gene.

4. The method of claim 1 wherein the inducible bacterial promoter is subject to thermal regulation.

5. The method of claim 4 wherein the thermal regulation is the result of a regulatory gene, which regulatory gene is the lacIts gene.

6. The method of claim 5 wherein the lacIts gene is located within the recombinant expression vector.

7. The method of claim 6 wherein the lacIts gene is in the same orientation as the T cell antigen receptor Vβ5.3 coding region to be expressed.

8. The method of claim 5, wherein the lacIts gene is located on a cotransformed vector.

9. The method of claim 5, wherein lacIts gene is located on a bacterial chromosome.

10. The method of claim 9 wherein the inducible bacterial promoter is selected from the group consisting of a lac promoter, a tac promoter, and a trc promoter.

11. The method of claim 10 wherein the inducible promoter is a trc promoter.

12. The method of producing a T cell antigen receptor Vβ5.3 protein of claim 11 wherein the recombinant expression vector further comprises a leader sequence.

13. The method of claim 12 wherein the leader sequence is selected from the group consisting of heat stable enterotoxin STII leader from *Escherichia coli* and a pelB leader from *Erwinia carotovora*.

14. The method of claim 13 wherein the leader sequence is the STII leader from *E. coli* or portion thereof.

15. The method of claim 14 wherein the leader sequence is a portion of the STII leader sequence of *E. coli* and the competent bacterial host cell is a cell which does not harbor the lacI of lacIq gene.

16. The method of claim 11 wherein the bacterial host cell is protease deficient.

17. The method according to claim 16, wherein the bacterial host cell is selected from the group consisting of SG22094, SG21163, and SG21173.

18. The method of claim 17, wherein the bacterial host cell is SG21173.

19. The method of producing a T cell antigen receptor Vβ5.3 protein of claim 1 wherein the recombinant expression vector comprises the following elements operably linked in a 5' to 3' orientation:
   a) trc promoter;
   b) a ribosome binding site;
   c) the T cell antigen receptor Vβ5.3 coding region;
   d) a transcription terminator;
   e) a lacIts regulatory gene sequence;
   f) a pBR322 origin of replication, and;
   g) a tetracycline resistance gene.

20. The method of claim 19 wherein the recombinant expression vector further comprises a leader sequence.

21. The method of claim 20 wherein the recombinant expression vector is selected from the group consisting of pK-Vβ5.3, pKT-Vβ5.3, pKTB-Vβ5.3, and pKB-Vβ5.3.

22. The method of 19 wherein the recombinant expression vector is selected from the group consisting of pKTBi-Vβ5.3, and pKBi-Vβ5.3.

23. An expression vector comprising an inducible bacterial promoter under the control of a lacIts regulatory gene, wherein said lacIts gene controls the expression of a coding region encoding a full-length T cell antigen receptor Vβ5.3 protein.

24. The expression vector of claim 23 wherein the inducible bacterial promoter is selected from the group consisting of a lac promoter, a tac promoter, and a trc promoter.

25. The expression vector of claim 23 wherein the inducible bacterial promoter is the trc promoter.

26. The expression vector of claim 25 which further comprises a leader sequence.

27. A bacterial cell transformed with the expression vector according to claim 23.

28. The expression vector of claim 23 wherein said vector is selected from the group consisting of pK-Vβ5.3, pKT-TVβ5.3, pKTB-Vβ5.3, pKTBi-Vβ5.3, and pKBi-Vβ5.3.

29. A process of producing a T cell antigen receptor Vβ5.3 protein comprising:
   a) inducing a bacterial host cell transformed with the expression vector according to claim 24 and;
   b) recovering T cell antigen receptor Vβ5.3 protein.

30. An expression vector which comprises in 5' to 3' direction;
   a) a trc promoter;
   b) a ribosome binding site;
   c) a coding region for a T cell antigen receptor Vβ5.3 protein;
   d) a transcription terminator;
   e) a lacIts regulatory gene sequence such that the transcription direction is the same as the Vβ5.3 coding sequence to be transcribed;
   f) a pBR322 origin of replication, and;
   g) a tetracycline resistance gene.

* * * * *

SEQUENCE LISTING ( 1 ) GENERAL INFORMATION:

( i i i ) NUMBER OF SEQUENCES:27

( 2 ) INFORMATION FOR SEQ ID NO: 1:

( i ) SEQUENCE CHARACTERISTICS:
        ( A ) LENGTH:34 base pairs
        ( B ) TYPE:nucleic acid
        ( C ) STRANDEDNESS:single
        ( D ) TOPOLOGY:linear ( i i ) MOLECULE TYPE:other nucleic acid
        ( A ) DESCRIPTION:synthetic oligonucleotide ( i i i ) HYPOTHETICAL:

( i v ) ANTI-SENSE:

( i x ) FEATURE:
        ( A ) NAME/KEY:
        ( B ) LOCATION:

( x i ) SEQUENCE DESCRIPTION: SEQ ID NO: 1:

```
TATAATGACT AGTCGCTGCA GCCAACCGCG GCTG                34
```

( 2 ) INFORMATION FOR SEQ ID NO: 2:

( i ) SEQUENCE CHARACTERISTICS:
        ( A ) LENGTH:23 base pairs
        ( B ) TYPE:nucleic acid
        ( C ) STRANDEDNESS:single
        ( D ) TOPOLOGY:linear ( i i ) MOLECULE TYPE:other nucleic acid
        ( A ) DESCRIPTION:synthetic oligonucleotide ( i i i ) HYPOTHETICAL:

( i v ) ANTI-SENSE:

( i x ) FEATURE:
        ( A ) NAME/KEY:
        ( B ) LOCATION:

( x i ) SEQUENCE DESCRIPTION: SEQ ID NO: 2:

GTCCTAGAGT ACTGAGCGGA TAC    23

( 2 ) INFORMATION FOR SEQ ID NO: 3:

( i ) SEQUENCE CHARACTERISTICS:
      ( A ) LENGTH:91 base pairs
      ( B ) TYPE:nucleic acid
      ( C ) STRANDEDNESS:single
      ( D ) TOPOLOGY:linear ( i i ) MOLECULE TYPE:other nucleic acid
      ( A ) DESCRIPTION:synthetic oligonucleotide ( i i i ) HYPOTHETICAL:

( i v ) ANTI-SENSE:

( i x ) FEATURE:
      ( A ) NAME/KEY:
      ( B ) LOCATION:

( x i ) SEQUENCE DESCRIPTION: SEQ ID NO: 3:

GGCTCGAGCC TAGGCTGCAG CCCGGGGCGC GCGCGGCCGC AGGCCTTTAA    50

TTAAGAGCTC CGGACCGCAC AATGTGGGCG CGCCCTTAAG A    91

( 2 ) INFORMATION FOR SEQ ID NO: 4:

( i ) SEQUENCE CHARACTERISTICS:
      ( A ) LENGTH:97 base pairs
      ( B ) TYPE:nucleic acid
      ( C ) STRANDEDNESS:single
      ( D ) TOPOLOGY:linear ( i i ) MOLECULE TYPE:other nucleic acid
      ( A ) DESCRIPTION:synthetic oligonucleotide ( i i i ) HYPOTHETICAL:

( i v ) ANTI-SENSE:

( i x ) FEATURE:
      ( A ) NAME/KEY:
      ( B ) LOCATION:

( x i ) SEQUENCE DESCRIPTION: SEQ ID NO: 4:

CTAGTCTTAA GGGCGCGCCC ACATTGTGCG GTCCGGAGCT CTTAATTAAA    50

GGCCTGCGGC CGCGCGCGCC CCGGGCTGCA GCCTAGGCTC GAGCCGC    97

( 2 ) INFORMATION FOR SEQ ID NO: 5:

( i ) SEQUENCE CHARACTERISTICS:
      ( A ) LENGTH:103 base pairs
      ( B ) TYPE:nucleic acid
      ( C ) STRANDEDNESS:single
      ( D ) TOPOLOGY:linear ( i i ) MOLECULE TYPE:other nucleic acid
      ( A ) DESCRIPTION:synthetic oligonucleotide ( i i i ) HYPOTHETICAL:

( i v ) ANTI-SENSE:

( i x ) FEATURE:
      ( A ) NAME/KEY:
      ( B ) LOCATION:

( x i ) SEQUENCE DESCRIPTION: SEQ ID NO: 5:

CTAGTAAATT CTATTTCAAG GAGACAGTCA TAATGAAATA CCTATTGCCT    50

```
      ACGGCAGCCG CTGGATTGTT ATTACTCGCT GCCCAACCAG CCATGGCCGA    100

GCT                                                       103
```

( 2 ) INFORMATION FOR SEQ ID NO: 6:

( i ) SEQUENCE CHARACTERISTICS:
        ( A ) LENGTH:95 base pairs
        ( B ) TYPE:nucleic acid
        ( C ) STRANDEDNESS:single
        ( D ) TOPOLOGY:linear ( i i ) MOLECULE TYPE:other nucleic acid
        ( A ) DESCRIPTION:synthetic oligonucleotide ( i i i ) HYPOTHETICAL:

( i v ) ANTI-SENSE:

( i x ) FEATURE:
        ( A ) NAME/KEY:
        ( B ) LOCATION:

( x i ) SEQUENCE DESCRIPTION: SEQ ID NO: 6:

```
      CGGCCATGGC TGGTTGGGCA GCGAGTAATA ACAATCCAGC GGCTGCCGTA    50

GGCAATAGGT ATTTCATTAT GACTGTCTCC TTGAAATAGA ATTTA         95
```

( 2 ) INFORMATION FOR SEQ ID NO: 7:

( i ) SEQUENCE CHARACTERISTICS:
        ( A ) LENGTH:105 base pairs
        ( B ) TYPE:nucleic acid
        ( C ) STRANDEDNESS:single
        ( D ) TOPOLOGY:linear ( i i ) MOLECULE TYPE:other nucleic acid
        ( A ) DESCRIPTION:synthetic oligonucleotide ( i i i ) HYPOTHETICAL:

( i v ) ANTI-SENSE:

( i x ) FEATURE:
        ( A ) NAME/KEY:
        ( B ) LOCATION:

( x i ) SEQUENCE DESCRIPTION: SEQ ID NO: 7:

```
      CTAGTAAATT CTATTTCAAG GAGACAGTCA TAATGAAAAA GAATATAGCA    50

TTCCTACTAG CTTCAATGTT CGTCTTCTCT ATTGCAACTA ACGCGTACGC    100

ACATT                                                     105
```

( 2 ) INFORMATION FOR SEQ ID NO: 8:

( i ) SEQUENCE CHARACTERISTICS:
        ( A ) LENGTH:98 base pairs
        ( B ) TYPE:nucleic acid
        ( C ) STRANDEDNESS:single
        ( D ) TOPOLOGY:linear ( i i ) MOLECULE TYPE:other nucleic acid
        ( A ) DESCRIPTION:synthetic oligonucleotide ( i i i ) HYPOTHETICAL:

( i v ) ANTI-SENSE:

( i x ) FEATURE:
        ( A ) NAME/KEY:
        ( B ) LOCATION:

( x i ) SEQUENCE DESCRIPTION: SEQ ID NO: 8:

```
GTGCGTACGC  GTTAGTTGCA  ATAGAGAAGA  CGAACATTGA  AGCTAGTAGG        50

AATGCTATAT  TCTTTTTCAT  TATGACTGTC  TCCTTGAAAT  AGAATTTA          98
```

( 2 ) INFORMATION FOR SEQ ID NO: 9:

( i ) SEQUENCE CHARACTERISTICS:
        ( A ) LENGTH:89 base pairs
        ( B ) TYPE:nucleic acid
        ( C ) STRANDEDNESS:single
        ( D ) TOPOLOGY:linear ( i i ) MOLECULE TYPE:other nucleic acid
        ( A ) DESCRIPTION:synthetic oligonucleotide ( i i i ) HYPOTHETICAL:

( i v ) ANTI-SENSE:

( i x ) FEATURE:
        ( A ) NAME/KEY:
        ( B ) LOCATION:

( x i ) SEQUENCE DESCRIPTION: SEQ ID NO: 9:

```
CTAGTCCGGA  ATTGGGCATC  GATTAACTTT  ATTATTAAAA  ATTAAAGAGG        50

TATATATTAA  TGTATCGATT  AAATAAGGAG  GAATAAATA                     89
```

( 2 ) INFORMATION FOR SEQ ID NO: 10:

( i ) SEQUENCE CHARACTERISTICS:
        ( A ) LENGTH:76 base pairs
        ( B ) TYPE:nucleic acid
        ( C ) STRANDEDNESS:single
        ( D ) TOPOLOGY:linear ( i i ) MOLECULE TYPE:other nucleic acid
        ( A ) DESCRIPTION:synthetic oligonucleotide ( i i i ) HYPOTHETICAL:

( i v ) ANTI-SENSE:

( i x ) FEATURE:
        ( A ) NAME/KEY:
        ( B ) LOCATION:

( x i ) SEQUENCE DESCRIPTION: SEQ ID NO: 10:

```
CTCCTTATTT  AATCGATACA  TTAATATATA  CCTCTTTAAT  TTTTAATAAT        50

AAAGTTAATC  GATGCCCAAT  TCCGGA                                    76
```

( 2 ) INFORMATION FOR SEQ ID NO: 11:

( i ) SEQUENCE CHARACTERISTICS:
        ( A ) LENGTH:71 base pairs
        ( B ) TYPE:nucleic acid
        ( C ) STRANDEDNESS:single
        ( D ) TOPOLOGY:linear ( i i ) MOLECULE TYPE:other nucleic acid
        ( A ) DESCRIPTION:synthetic oligonucleotide ( i i i ) HYPOTHETICAL:

( i v ) ANTI-SENSE:

( i x ) FEATURE:
        ( A ) NAME/KEY:
        ( B ) LOCATION:

( x i ) SEQUENCE DESCRIPTION: SEQ ID NO: 11:

```
ATGAAATACC  TATTGCCTAC  GGCAGCCGCT  GGATTGTTAT  TACTCGCTGC        50
```

CCAACCAGCC ATGGCCGAGC T 71

(2) INFORMATION FOR SEQ ID NO: 12:

(i) SEQUENCE CHARACTERISTICS:
        (A) LENGTH:76 base pairs
        (B) TYPE:nucleic acid
        (C) STRANDEDNESS:single
        (D) TOPOLOGY:linear (ii) MOLECULE TYPE:other nucleic acid
        (A) DESCRIPTION:synthetic oligonucleotide (iii) HYPOTHETICAL:

(iv) ANTI-SENSE:

(ix) FEATURE:
        (A) NAME/KEY:
        (B) LOCATION:

(xi) SEQUENCE DESCRIPTION: SEQ ID NO: 12:

CGGCCATGGC TGGTTGGGCA GCGAGTAATA ACAATCCAGC GGCTGCCGTA 50

GGCAATAGGT ATTTCATTAT TTATTC 76

(2) INFORMATION FOR SEQ ID NO: 13:

(i) SEQUENCE CHARACTERISTICS:
        (A) LENGTH:73 base pairs
        (B) TYPE:nucleic acid
        (C) STRANDEDNESS:single
        (D) TOPOLOGY:linear (ii) MOLECULE TYPE:other nucleic acid
        (A) DESCRIPTION:synthetic oligonucleotide (iii) HYPOTHETICAL:

(iv) ANTI-SENSE:

(ix) FEATURE:
        (A) NAME/KEY:
        (B) LOCATION:

(xi) SEQUENCE DESCRIPTION: SEQ ID NO: 13:

ATGAAAAAGA ATATAGCATT CCTACTAGCT TCAATGTTCG TCTTCTCTAT 50

TGCAACTAAC GCGTACGCAC ATT 73

(2) INFORMATION FOR SEQ ID NO: 14:

(i) SEQUENCE CHARACTERISTICS:
        (A) LENGTH:79 base pairs
        (B) TYPE:nucleic acid
        (C) STRANDEDNESS:single
        (D) TOPOLOGY:linear (ii) MOLECULE TYPE:other nucleic acid
        (A) DESCRIPTION:synthetic oligonucleotide (iii) HYPOTHETICAL:

(iv) ANTI-SENSE:

(ix) FEATURE:
        (A) NAME/KEY:
        (B) LOCATION:

(xi) SEQUENCE DESCRIPTION: SEQ ID NO: 14:

GTGCGTACGC GTTAGTTGCA ATAGAGAAGA CGAACATTGA AGCTAGTAGG 50

AATGCTATAT TCTTTTTCAT TATTTATTC 79

( 2 ) INFORMATION FOR SEQ ID NO: 15:

( i ) SEQUENCE CHARACTERISTICS:
        ( A ) LENGTH:33 base pairs
        ( B ) TYPE:nucleic acid
        ( C ) STRANDEDNESS:single
        ( D ) TOPOLOGY:linear ( i i ) MOLECULE TYPE:other nucleic acid
        ( A ) DESCRIPTION:synthetic oligonucleotide ( i i i ) HYPOTHETICAL:

( i v ) ANTI-SENSE:

( i x ) FEATURE:
        ( A ) NAME/KEY:
        ( B ) LOCATION:

( x i ) SEQUENCE DESCRIPTION: SEQ ID NO: 15:

```
TAATTAGCCA TGGCCGGCGT AACCCAATCT CCG                33
```

( 2 ) INFORMATION FOR SEQ ID NO: 16:

( i ) SEQUENCE CHARACTERISTICS:
        ( A ) LENGTH:21 base pairs
        ( B ) TYPE:nucleic acid
        ( C ) STRANDEDNESS:single
        ( D ) TOPOLOGY:linear ( i i ) MOLECULE TYPE:other nucleic acid
        ( A ) DESCRIPTION:synthetic oligonucleotide ( i i i ) HYPOTHETICAL:

( i v ) ANTI-SENSE:

( i x ) FEATURE:
        ( A ) NAME/KEY:
        ( B ) LOCATION:

( x i ) SEQUENCE DESCRIPTION: SEQ ID NO: 16:

```
CCAGTGCCAA GCTTGCATGC C                             21
```

( 2 ) INFORMATION FOR SEQ ID NO: 17:

( i ) SEQUENCE CHARACTERISTICS:
        ( A ) LENGTH:34 base pairs
        ( B ) TYPE:nucleic acid
        ( C ) STRANDEDNESS:single
        ( D ) TOPOLOGY:linear ( i i ) MOLECULE TYPE:other nucleic acid
        ( A ) DESCRIPTION:synthetic oligonucleotide ( i i i ) HYPOTHETICAL:

( i v ) ANTI-SENSE:

( i x ) FEATURE:
        ( A ) NAME/KEY:
        ( B ) LOCATION:

( x i ) SEQUENCE DESCRIPTION: SEQ ID NO: 17:

```
GAAATTAACG CGTACGCAGG CGTAACCCAA TCTC               34
```

( 2 ) INFORMATION FOR SEQ ID NO: 18:

( i ) SEQUENCE CHARACTERISTICS:
        ( A ) LENGTH:21 base pairs
        ( B ) TYPE:nucleic acid
        ( C ) STRANDEDNESS:single (D) TOPOLOGY:linear (i i) MOLECULE TYPE:other nucleic acid
    (A) DESCRIPTION:synthetic oligonucleotide (i i i) HYPOTHETICAL:

(i v) ANTI-SENSE:

(i x) FEATURE:
    (A) NAME/KEY:
    (B) LOCATION:

(x i) SEQUENCE DESCRIPTION: SEQ ID NO: 18:

CCAGTGCCAA GCTTGCATGC C                                               21

(2) INFORMATION FOR SEQ ID NO: 19:

(i) SEQUENCE CHARACTERISTICS:
        (A) LENGTH:110 base pairs
        (B) TYPE:nucleic acid
        (C) STRANDEDNESS:single
        (D) TOPOLOGY:linear (i i) MOLECULE TYPE:other nucleic acid
        (A) DESCRIPTION:synthetic oligonucleotide (i i i) HYPOTHETICAL:

(i v) ANTI-SENSE:

(i x) FEATURE:
        (A) NAME/KEY:
        (B) LOCATION:

(x i) SEQUENCE DESCRIPTION: SEQ ID NO: 19:

CTAGTCCGGA ATTGGGCATC GATTAACTTT ATTATTAAAA ATTAAAGAGG    50

TATATATTAA TGTATCGATT AAATAAGGAG GAATAAACCA TGGCACATTG   100

TGCGGTCCGC                                               110

(2) INFORMATION FOR SEQ ID NO: 20:

(i) SEQUENCE CHARACTERISTICS:
        (A) LENGTH:110 base pairs
        (B) TYPE:nucleic acid
        (C) STRANDEDNESS:single
        (D) TOPOLOGY:linear (i i) MOLECULE TYPE:other nucleic acid
        (A) DESCRIPTION:synthetic oligonucleotide (i i i) HYPOTHETICAL:

(i v) ANTI-SENSE:

(i x) FEATURE:
        (A) NAME/KEY:
        (B) LOCATION:

(x i) SEQUENCE DESCRIPTION: SEQ ID NO: 20:

CCGGGCGGAC CGCACAATGT GCCATGGTTT ATTCCTCCTT ATTTAATCGA    50

TACATTAATA TATACCTCTT TAATTTTTAA TAATAAAGTT AATCGATGCC   100

CAATTCCGGA                                               110

(2) INFORMATION FOR SEQ ID NO: 21:

(i) SEQUENCE CHARACTERISTICS:
        (A) LENGTH:42 base pairs
        (B) TYPE:nucleic acid
        (C) STRANDEDNESS:single (D) TOPOLOGY:linear (ii) MOLECULE TYPE:other nucleic acid
    (A) DESCRIPTION:synthetic oligonucleotide (iii) HYPOTHETICAL:

(iv) ANTI-SENSE:

(ix) FEATURE:
    (A) NAME/KEY:
    (B) LOCATION:

(xi) SEQUENCE DESCRIPTION: SEQ ID NO: 21:

```
CTAGTAAATT ATATTTAAAG GAGGAATAAA CCATGGCACA TT            42
```

(2) INFORMATION FOR SEQ ID NO: 22:

(i) SEQUENCE CHARACTERISTICS:
        (A) LENGTH:35 base pairs
        (B) TYPE:nucleic acid
        (C) STRANDEDNESS:single
        (D) TOPOLOGY:linear (ii) MOLECULE TYPE:other nucleic acid
        (A) DESCRIPTION:synthetic oligonucleotide (iii) HYPOTHETICAL:

(iv) ANTI-SENSE:

(ix) FEATURE:
        (A) NAME/KEY:
        (B) LOCATION:

(xi) SEQUENCE DESCRIPTION: SEQ ID NO: 22:

```
GTGCCATGGT TTATTCCTCC TTTAAATATA ATTTA                    35
```

(2) INFORMATION FOR SEQ ID NO: 23:

(i) SEQUENCE CHARACTERISTICS:
        (A) LENGTH:20 base pairs
        (B) TYPE:nucleic acid
        (C) STRANDEDNESS:single
        (D) TOPOLOGY:linear (ii) MOLECULE TYPE:other nucleic acid
        (A) DESCRIPTION:synthetic oligonucleotide (iii) HYPOTHETICAL:

(iv) ANTI-SENSE:

(ix) FEATURE:
        (A) NAME/KEY:
        (B) LOCATION:

(xi) SEQUENCE DESCRIPTION: SEQ ID NO: 23:

```
TATAGTCCAT GGGCGTAACC                                     20
```

(2) INFORMATION FOR SEQ ID NO: 24:

(i) SEQUENCE CHARACTERISTICS:
        (A) LENGTH:25 base pairs
        (B) TYPE:nucleic acid
        (C) STRANDEDNESS:single
        (D) TOPOLOGY:linear (ii) MOLECULE TYPE:other nucleic acid
        (A) DESCRIPTION:synthetic oligonucleotide (iii) HYPOTHETICAL:

(iv) ANTI-SENSE:

( i x ) FEATURE:
  ( A ) NAME/KEY:
  ( B ) LOCATION:

( x i ) SEQUENCE DESCRIPTION: SEQ ID NO: 24:

AACTTCCCGG GTTATCATTA GCTGC               25

( 2 ) INFORMATION FOR SEQ ID NO: 25:

( i ) SEQUENCE CHARACTERISTICS:
  ( A ) LENGTH:276 base pairs
  ( B ) TYPE:nucleic acid
  ( C ) STRANDEDNESS:single
  ( D ) TOPOLOGY:linear ( i i ) MOLECULE TYPE:cDNA ( i i i ) HYPOTHETICAL:

( i v ) ANTI-SENSE:

( i x ) FEATURE:
  ( A ) NAME/KEY:
  ( B ) LOCATION:

( x i ) SEQUENCE DESCRIPTION: SEQ ID NO: 25:

| GGC | GTA | ACC | CAA | TCT | CCG | ACT | CAC | CTG | ATC | AAA | ACG | AGA | 39 |
| GGA | CAG | CAC | GTG | ACT | CTG | AGA | TGC | TCT | CCT | ATC | TCT | GGG | 78 |
| CAC | AAG | AGT | GTG | TCC | TGG | TAC | CAA | CAG | GTC | CTG | GGT | CAG | 117 |
| GGG | CCC | CAG | TTT | ATC | TTT | CAG | TAT | TAT | GAG | AAA | GAA | GAG | 156 |
| AGA | GGA | AGA | GGA | AAC | TTC | CCT | GAT | CGA | TTC | TCA | GCT | CGC | 195 |
| CAG | TTC | CCT | AAC | TAT | AGC | TCT | GAG | CTG | AAT | GTG | AAC | GCC | 234 |
| TTG | TTG | CTG | GGG | GAC | TCG | GCC | CTG | TAT | CTC | TGT | GCC | AGC | 273 |
| AGC | | | | | | | | | | | | | 276 |

( 2 ) INFORMATION FOR SEQ ID NO: 26:

( i ) SEQUENCE CHARACTERISTICS:
  ( A ) LENGTH:276 base pairs
  ( B ) TYPE:nucleic acid
  ( C ) STRANDEDNESS:single
  ( D ) TOPOLOGY:linear ( i i ) MOLECULE TYPE:cDNA ( i i i ) HYPOTHETICAL:

( i v ) ANTI-SENSE:

( i x ) FEATURE:
  ( A ) NAME/KEY:
  ( B ) LOCATION:

( x i ) SEQUENCE DESCRIPTION: SEQ ID NO: 26:

| CCG | CAT | TGG | GTT | AGA | GGC | TGA | GTG | GAC | TAG | TTT | TGC | TCT | 39 |
| CCT | GTC | GTG | CAC | TGA | GAC | TCT | ACG | AGA | GGA | TAG | AGA | CCC | 78 |
| GTG | TTC | TCA | CAC | AGG | ACC | ATG | GTT | GTC | CAG | GAC | CCA | GTC | 117 |
| CCC | GGG | GTC | AAA | TAG | AAA | GTC | ATA | ATA | CTC | TTT | CTT | CTC | 156 |
| TCT | CCT | TCT | CCT | TTG | AAG | GGA | CTA | GCT | AAG | AGT | CGA | GCG | 195 |
| GTC | AAG | GGA | TTG | ATA | TCG | AGA | CTC | GAC | TTA | CAC | TTG | CGG | 234 |
| AAC | AAC | GAC | CCC | CTG | AGC | CGG | GAC | ATA | GAG | ACA | CGG | TCG | 273 |

TCG

276

(2) INFORMATION FOR SEQ ID NO: 27:

(i) SEQUENCE CHARACTERISTICS:
     (A) LENGTH:92 amino acids
     (B) TYPE:amino acid
     (C) STRANDEDNESS:single
     (D) TOPOLOGY:linear (ii) MOLECULE TYPE:protein (iii) HYPOTHETICAL:

(iv) ANTI-SENSE:

(ix) FEATURE:
     (A) NAME/KEY:
     (B) LOCATION:

(xi) SEQUENCE DESCRIPTION: SEQ ID NO: 27:

```
Gly Val Thr Gln Ser Pro Thr His Leu Ile Lys Thr Arg Gly Gln
 1               5                  10                  15

His Val Thr Leu Arg Cys Ser Pro Ile Ser Gly His Lys Ser Val
                20                  25                  30

Ser Trp Tyr Gln Gln Val Leu Gly Gln Gly Pro Gln Phe Ile Phe
                35                  40                  45

Gln Tyr Tyr Glu Lys Glu Glu Arg Gly Arg Gly Asn Phe Pro Asp
                50                  55                  60

Arg Phe Ser Ala Arg Gln Phe Pro Asn Tyr Ser Ser Glu Leu Asn
                65                  70                  75

Val Asn Ala Leu Leu Leu Gly Asp Ser Ala Leu Tyr Leu Cys Ala
                80                  85                  90

Ser Ser
 92
```